(12) United States Patent
Yamazaki et al.

(10) Patent No.: US 10,842,349 B2
(45) Date of Patent: Nov. 24, 2020

(54) ENDOSCOPE OPERATION SUPPORT SYSTEM

(71) Applicant: SEIKO EPSON CORPORATION, Tokyo (JP)

(72) Inventors: Akio Yamazaki, Matsumoto (JP); Yuichi Mori, Minowa-machi (JP)

(73) Assignee: SEIKO EPSON CORPORATION, Tokyo (JP)

( * ) Notice: Subject to any disclaimer, the term of this patent is extended or adjusted under 35 U.S.C. 154(b) by 6 days.

(21) Appl. No.: 15/875,507

(22) Filed: Jan. 19, 2018

(65) Prior Publication Data

US 2018/0214007 A1 Aug. 2, 2018

(30) Foreign Application Priority Data

Jan. 30, 2017 (JP) .................................. 2017-013814

(51) Int. Cl.
*G06T 7/70* (2017.01)
*H04N 5/232* (2006.01)
(Continued)

(52) U.S. Cl.
CPC ...... *A61B 1/00045* (2013.01); *A61B 1/00009* (2013.01); *A61B 1/00048* (2013.01); *A61B 1/05* (2013.01); *A61B 5/06* (2013.01); *A61B 5/1455* (2013.01); *G02B 27/0172* (2013.01); *G06T 7/70* (2017.01); *G06T 19/003* (2013.01); *H04N 5/22525* (2018.08); *H04N 5/23258* (2013.01); *H04N 5/23293* (2013.01); *H04N 5/272* (2013.01); *G02B 2027/014* (2013.01); (Continued)

(58) Field of Classification Search
None
See application file for complete search history.

(56) References Cited

U.S. PATENT DOCUMENTS 7,233,820 B2 * 6/2007 Gilboa .................. A61B 5/065
600/427
8,594,862 B2 11/2013 Callou et al.
(Continued)

FOREIGN PATENT DOCUMENTS

JP 2004-016282 A 1/2004
JP 4098535 B2 6/2008
(Continued)

*Primary Examiner* — Kate H Luo
(74) *Attorney, Agent, or Firm* — Oliff PLC

(57) ABSTRACT

An endoscope operation support system includes: an image display unit which, transmits external scenery and allows the user to visually recognize the external scenery, and also displays a virtual image as superimposed on the external scenery and allows the user to visually recognize the virtual image; a control unit which controls the image display unit; an endoscope unit having an image pickup unit at a distal end part inserted in an image pickup target part of an object, the image pickup unit picking up an image inside the image pickup target part; and a position detection unit which detects a position of the distal end part. The control unit causes the image display unit to display a position display image including a pointer image indicating the position of the distal end part detected by the position detection unit, as the virtual image superimposed on the object in the external scenery.

13 Claims, 18 Drawing Sheets

(51) Int. Cl.
*H04N 5/272* (2006.01)
*H04N 5/225* (2006.01)
*A61B 1/00* (2006.01)
*G06T 19/00* (2011.01)
*G02B 27/01* (2006.01)
*A61B 1/05* (2006.01)
*A61B 5/06* (2006.01)
*A61B 5/1455* (2006.01)

(52) U.S. Cl.
CPC ........ *G02B 2027/0132* (2013.01); *G02B 2027/0138* (2013.01); *G02B 2027/0141* (2013.01); *G02B 2027/0147* (2013.01); *G02B 2027/0178* (2013.01); *G06T 2207/10068* (2013.01); *G06T 2219/028* (2013.01); *H04N 2005/2255* (2013.01)

(56) References Cited

U.S. PATENT DOCUMENTS

| | | | |
|---|---|---|---|
| 10,388,066 B2 * | 8/2019 | Averbuch | A61B 5/066 |
| 2005/0033117 A1 * | 2/2005 | Ozaki | A61B 5/062 |
| | | | 600/109 |
| 2006/0281971 A1 | 12/2006 | Sauer et al. | |
| 2009/0034820 A1 * | 2/2009 | Sugiyama | A61B 6/5235 |
| | | | 382/132 |
| 2009/0207241 A1 * | 8/2009 | Igarashi | A61B 1/042 |
| | | | 348/68 |
| 2009/0274271 A1 * | 11/2009 | Pfister | A61B 90/13 |
| | | | 378/62 |
| 2011/0060185 A1 * | 3/2011 | Ikuma | A61B 5/7214 |
| | | | 600/104 |
| 2011/0273549 A1 * | 11/2011 | Kase | A61B 1/00177 |
| | | | 348/68 |
| 2012/0169858 A1 * | 7/2012 | Nakano | A61B 1/00147 |
| | | | 348/65 |
| 2014/0018623 A1 * | 1/2014 | Gono | A61B 1/05 |
| | | | 600/109 |
| 2014/0142381 A1 * | 5/2014 | Bae | G02B 23/2484 |
| | | | 600/109 |
| 2014/0253685 A1 * | 9/2014 | Akimoto | A61B 1/05 |
| | | | 348/45 |
| 2015/0057498 A1 | 2/2015 | Akimoto et al. | |
| 2015/0216392 A1 | 8/2015 | Tojo et al. | |
| 2015/0317830 A1 | 11/2015 | Kihara et al. | |
| 2015/0363979 A1 | 12/2015 | Takano et al. | |
| 2016/0154620 A1 * | 6/2016 | Tsuda | G02B 27/017 |
| | | | 345/633 |

FOREIGN PATENT DOCUMENTS

| | | |
|---|---|---|
| JP | 2013-144539 A | 7/2013 |
| JP | 2014-131551 A | 7/2014 |
| JP | 2015-099184 A | 5/2015 |
| JP | 2016-032485 A | 3/2016 |
| WO | 2014/061566 A1 | 4/2014 |
| WO | 2014/141968 A1 | 9/2014 |
| WO | WO 2015/008470 A2 * | 1/2015 |

* cited by examiner

ENDOSCOPE OPERATION SUPPORT SYSTEM

BACKGROUND

1. Technical Field

The present invention relates to a system for supporting the operation of an endoscope.

2. Related Art

JP-A-2013-144539 discloses a head-mounted display device which enables the user to simultaneously visually recognize a real image of an object in the direction of the field of vision and information not expressed in the appearance of the object, without moving the line of sight.

For example, in the case of inspecting a tubular organ of a subject, such as the esophagus, stomach, or intestine, using an endoscope, an image of a part that is being shot by the endoscope inside the organ can be confirmed on a monitor. Therefore, traditionally, based on the image displayed on the monitor, the operator of the endoscope presumes the current position where the image is being shot. However, from the appearance of the subject, the operator cannot know the current position where the image is actually being shot inside the organ within the subject. Thus, it is desired that, during the operation of the endoscope, the operator should enable to confirm the current position from the appearance of the subject in addition to enabling to confirm the image of the part that is being shot, and thus enable to operate the endoscope while confirming the state of the subject, thereby improving the certainty and safety of the operation of the endoscope. This problem is not limited to the endoscope used for inspecting inside organs of a living body but also applies to endoscopes used for inspecting inside various artificial objects such as water pipe, gas pipe, and electricity pipe within a building or the like.

With the head-mounted display device disclosed in JP-A-2013-144539, it is possible to visually recognize a hand (object) included in the external scenery and a virtual image based on an X-ray image (superimposition information to superimpose invisible information), which is information not expressed in the appearance of a hand, in such a way that the virtual image is superimposed on the hand. However, JP-A-2013-144539 discloses no technique for detecting the current position of a part whose image is being shot inside a target object being inspected with the endoscope and enabling the confirmation of the current position of the part whose image is being shot.

SUMMARY

An advantage of some aspects of the invention is to solve at least a part of the problems described above, and the invention can be implemented in the following configurations.

(1) According to an aspect of the invention, an endoscope operation support system is provided. The endoscope operation support system includes: an image display unit which, in the state of being mounted on a head of a user, transmits external scenery and allows the user to visually recognize the external scenery, and also displays a virtual image as superimposed on the external scenery and allows the user to visually recognize the virtual image; a control unit which controls the image display unit; an endoscope unit having an image pickup unit at a distal end part inserted in an image pickup target part of an object, the image pickup unit picking up an image inside the image pickup target part; and a position detection unit which detects a position of the distal end part inserted in the image pickup target part. The control unit causes the image display unit to display a position display image including a pointer image indicating the position of the distal end part detected by the position detection unit, as the virtual image superimposed on the object included in the external scenery.

With the endoscope operation support system of this configuration, the position detection unit can detect the position of the distal end part of the endoscope unit inserted in the image pickup target part of the object. The image display unit can display, as a virtual image, the position display image including the pointer image indicating the position of the distal end part detected by the position detection unit, the position display image being superimposed on the object included in the external scenery visually recognized by the user. Thus, the user of an endoscope device having the endoscope unit can operate the endoscope device while confirming which position in the appearance of the object the position where the image pickup unit is picking up an image corresponds to. Therefore, the certainty and safety of the operation of the endoscope device can be improved.

(2) In the endoscope operation support system of the configuration described in (1), the distal end part may have a motion sensor for detecting a movement of the distal end part. The position detection unit may find the position of the distal end part, using an amount of movement and a direction of movement of the distal end part found from a sensor value of the motion sensor. The control unit may cause the position display image to be displayed as superimposed on the object at a position on the object corresponding to the position of the distal end part found by the position detection unit.

With the endoscope operation support system of this configuration, the position of the distal end part can be detected from the sensor value of the motion sensor for detecting the movement of the distal end part. The position display image can be displayed as superimposed on the object at the position on the object corresponding to the detected position of the distal end part.

(3) In the endoscope operation support system of the configuration described in (1), the position detection unit may find the position of the distal end part from an amount of change of a position of a feature point included in a picked-up image picked up by the image pickup unit. The control unit may cause the position display image to be displayed as superimposed on the object at a position on the object corresponding to the position of the distal end part found by the position detection unit.

With the endoscope operation support system of this configuration, too, the position of the distal end part can be detected from the amount of change of the position of the feature point included in the picked-up image. The position display image can be displayed as superimposed on the object at the position on the object corresponding to the detected position of the distal end part.

(4) The endoscope operation support system of the configuration described in (1) may include an amount-of-insertion detection unit which detects an amount of insertion of the distal end part into the image pickup target part. The position detection unit may find the position of the distal end part from the amount of insertion. The control unit may cause the position display image to be displayed as superimposed on the object at a position on the object corresponding to the position of the distal end part found by the position detection unit.

With the endoscope operation support system of this configuration, too, the position of the distal end part can be detected from the amount of insertion of the distal end part into the image pickup target part. The position display image can be displayed as superimposed on the object at the position on the object corresponding to the detected position of the distal end part.

(5) In the endoscope operation support system of the configuration described in (3) or (4), the position detection unit may detect a direction of a distal end surface of the distal end part, based on a positional relationship between a center position of a picked-up image picked up by the image pickup unit and a forward movement site image showing a site where a forward movement can be made, included in the picked-up image.

With the endoscope operation support system of this configuration, the direction of image pickup by the image pickup unit corresponding to the direction of the distal end surface of the distal end part can be easily detected.

(6) In the endoscope operation support system of the foregoing configurations, the control unit may decide a display position of the position display image in the image display unit, based on a position of the image pickup target part corresponding to a position of the object included in a field of vision of the user, and the detected position of the distal end part.

With the endoscope operation support system of this configuration, the display position of the position display image in the image display unit can be decided, based on the position of the image pickup target part corresponding to the position of the object included in the field of vision of the user, and the detected position of the distal end part, and the position display image can be displayed as superimposed on the object at the position on the object corresponding to the position of the distal end part.

(7) The endoscope operation support system of the foregoing configurations may include an image pickup target part data creation unit which creates image pickup target part data expressing a structure of the image pickup target part, using the position of the distal end part detected by the position detection unit and a picked-up image picked up at the position of the distal end part.

With the endoscope operation support system of this configuration, the image pickup target part data expressing the structure of the image pickup target part can be created using the picked-up image. Also, the image pickup target part data thus created can be used for various kinds of processing such as image analysis.

(8) In the endoscope operation support system of the foregoing configurations, the image pickup target part may be a part that is not shown in an appearance of the object. The position display image may include the pointer image, an image pickup target part image showing the image pickup target part within a range that satisfies a predetermined condition including the position of the distal end part, and a direction image showing a direction of image pickup by the image pickup unit.

With the endoscope operation support system of this configuration, the image pickup target part image and the direction image are displayed in addition to the pointer image, as the position display image. Therefore, the position of the distal end part and the direction of image pickup with respect to the image pickup target part can be intuitively confirmed. Thus, the certainty and safety of the operation of the endoscope can be improved further.

(9) In the endoscope operation support system of the configuration described in (8), the image pickup target part image may be created using standard image pickup target part data showing a standard structure of the image pickup target part that is prepared in advance.

With the endoscope operation support system of this configuration, the image pickup target part image can be easily created using the standard image pickup target part data, and the image pickup target part image can be displayed as a part of the position display image.

(10) In the endoscope operation support system of the configuration described in (8) according to the configuration described in (7), before the image pickup target part data is created, the image pickup target part image may be created using standard image pickup target part data showing a standard structure of the image pickup target part that is prepared in advance, whereas in the case where the image pickup target part data is created, the image pickup target part image may be created using updated image pickup target part data every time the created image pickup target part data is updated.

With the endoscope operation support system of this configuration, the image pickup target part image created using the image pickup target part data corresponding to the actual structure of the image pickup target part can be displayed as a part of the position display image. Therefore, the sense of reality in the operation of the endoscope device having the endoscope unit can be enhanced.

(11) In the endoscope operation support system of the foregoing configurations, the control unit may cause the image display unit to display, as the virtual image, a picked-up image picked up by the image pickup unit at the position of the distal end part, in addition to the position display image.

With the endoscope operation support system of this configuration, the user can operate the endoscope device having the endoscope unit while confirming the position of the distal end part from the appearance of the object based on the position display image and also visually recognizing the picked-up image picked up at that position. Thus, the certainty and safety of the operation of the endoscope device can be improved further.

(12) In the endoscope operation support system of the configuration described in (11), the control unit may cause the image display unit to display the picked-up image at a position that does not overlap with the position display image.

With the endoscope operation support system of this configuration, the picked-up image can be visually recognized without reducing the visibility of the position display image to the user.

(13) In the endoscope operation support system of the configuration described in (11) or (12), the control unit may switch from a see-through mode in which the position display image and the picked-up image are displayed as the virtual image superimposed on the external scenery, to a full-screen mode in which the picked-up image is displayed on a full screen, if the head is in a still state where the head remains still for a predetermined time, and the control unit may switch to the see-through mode if the head is no longer in the still state.

If the head of the user is in the still state, the user is presumed to be gazing at the position of the distal end part in the image pickup target part. Therefore, in this case, the full-screen mode, in which the picked-up image is displayed on the full screen, is automatically started. Thus, the user can gaze at details of the picked-up image displayed on the full screen.

(14) In the endoscope operation support system of the configuration described in one of (11) to (13), the control unit may switch between a see-through mode in which the position display image and the picked-up image are displayed as the virtual image superimposed on the external scenery and a full-screen mode in which the picked-up image is displayed on a full screen, in response to a mode switch instruction.

With the endoscope operation support system of this configuration, in the case where the user gazes at the position of the distal end part of the image pickup target part, the display mode is switched to the full-screen mode, in which the picked-up image is displayed on the screen full. Thus, the user can gaze at details of the picked-up image displayed on the full screen.

The invention can also be realized in various forms other than the endoscope operation support system. For example, the invention can be realized in the form of an endoscope operation support method, a head-mounted display device, an endoscope device, a control method for a head-mounted display device, a control method for an endoscope device, a computer program for realizing the functions of components provided in a head-mounted display device, a recording medium with the computer program recorded therein, a computer program for realizing the functions of components provided in an endoscope device, a recording medium with the computer program recorded therein, and the like.

BRIEF DESCRIPTION OF THE DRAWINGS

The invention will be described with reference to the accompanying drawings, wherein like numbers reference like elements.

DESCRIPTION OF EXEMPLARY EMBODIMENTS

A. First Embodiment

A1. Configuration of Endoscope Operation Support System

Figure 1:
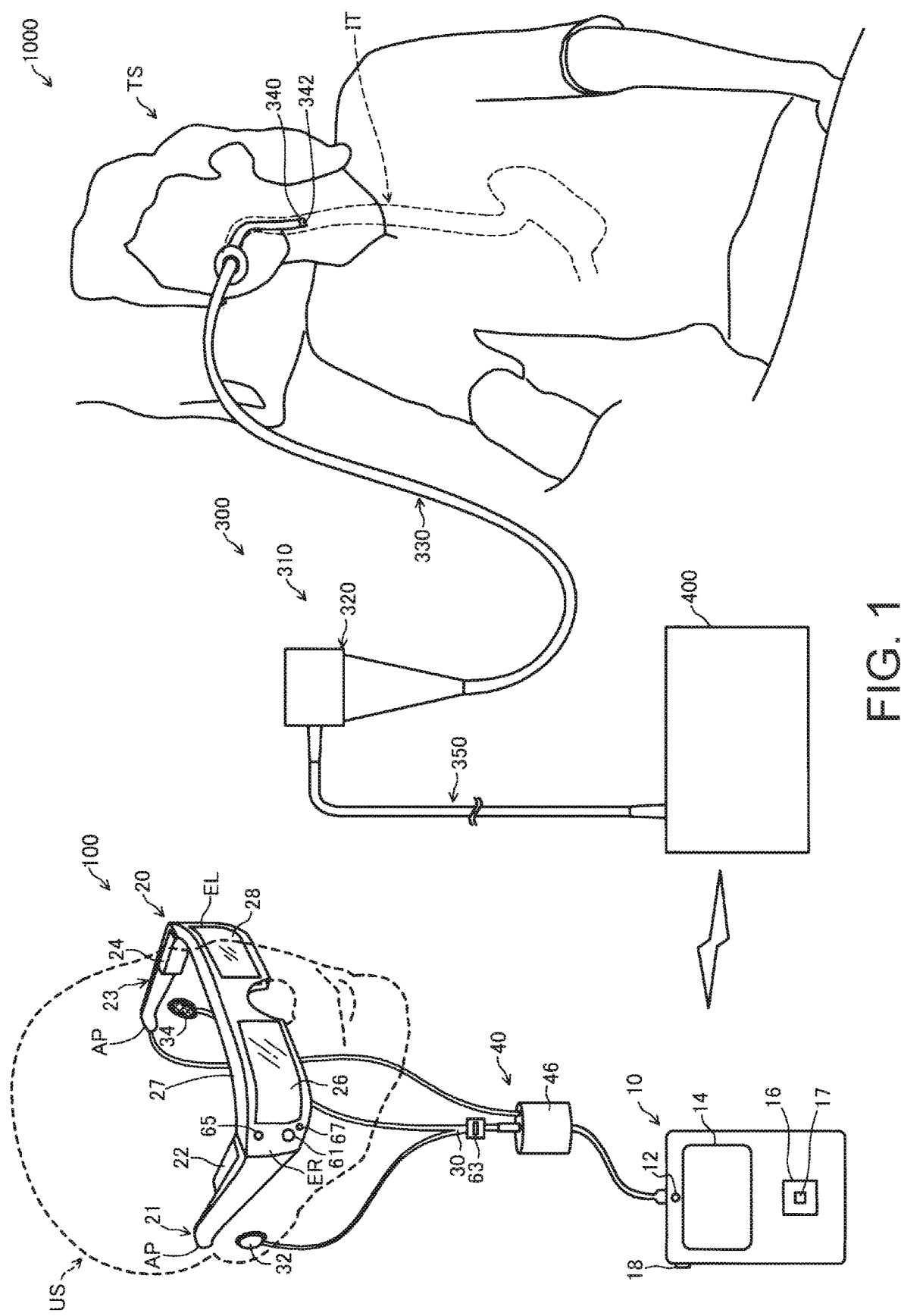
FIG. 1 is an explanatory view showing the schematic configuration of an endoscope operation support system according to a first embodiment.

FIG. 1 is an explanatory view showing the schematic configuration of an endoscope operation support system according to a first embodiment of the invention. An endoscope operation support system 1000 includes a head-mounted display device 100 and an endoscope device 300. The head-mounted display device 100 provides information for supporting the operation of the endoscope device 300 as an image to the user of the head-mounted display device 100, as will be described later.

The head-mounted display device 100 is a display device mounted on the head of the user and is also called HMD (head-mounted display). The HMD 100 is a see-through (transmission-type) head-mounted display device which allows an image to emerge in an external field that is transmitted through glasses and thus visually recognized. In this example, the user is the operator operating the endoscope device 300.

The HMD 100 has an image display unit 20 which allows the user to visually recognize an image, and a control device (controller) 10 which controls the image display unit 20. The endoscope device 300 has an endoscope unit 310 and an endoscope control device 400. The control device 10 of the HMD 100 and the endoscope control device 400 of the endoscope device 300 are connected to each other via a wireless or wired communication channel. In this example, these devices are connected together via a wireless communication channel, as will be described later.

The endoscope unit 310 of the endoscope device 300 has an operation part 320, an insertion part 330, and a connection part 350. An image pickup unit 342, or an illumination lens, forceps opening, nozzle or the like, not illustrated, is provided at a distal end part 340 of the cable-like insertion part 330. In this embodiment, the tubular organs from the oral cavity to the anus of a subject TS (in FIG. 1, the oral cavity to the stomach are indicated by dashed lines) are an image pickup target part IT. The image pickup unit 342 picks up an image inside the image pickup target part IT at the position of the distal end part 340 inserted in the image pickup target part (tubular organs) IT. The operation part 320 is provided with an angle knob for controlling the direction of the distal end part 340 and various operation buttons (not illustrated). By operating these, the user carries out image pickup with the image pickup unit 342, feeding/suction of air or water, operation of the forceps, and the like. The connection part 350 is connected between the operation part 320 and the endoscope control device 400. Transmission of picked-up image data or the like from the image pickup unit 342 to the endoscope control device 400, supply of illumination light from the endoscope control device 400, feeding of air or water to the nozzle at the distal end part 340, suction of air or water from the forceps opening, and the like are carried out via the connection part 350. The endoscope control device 400 will be described later.

The image display unit 20 of the HMD 100 is a wearing body to be mounted on the head of the user and is in the form of eyeglasses in this embodiment. The image display unit 20 has a main body configured of a right holding part 21, a left holding part 23, and a front frame 27. The main body includes a right display unit 22, a left display unit 24, a right light guide plate 26, and a left light guide plate 28.

The right holding part 21 and the left holding part 23 each extend backward from both ends of the front frame 27 and hold the image display unit 20 on the head of the user, like the temples of eyeglasses. Of the two ends of the front frame 27, the end part situated on the right-hand side of the user when the user is wearing the image display unit 20 is referred to as an end part ER, and the end part situated on the left-hand side of the user is referred to as an end part EL. The right holding part 21 is provided, extending from the end part ER of the front frame 27 to a position corresponding to the right temporal region of the user when the user is wearing the image display unit 20. The left holding part 23 is provided, extending from the end part EL of the front frame 27 to the left temporal region of the user when the user is wearing the image display unit 20.

The right light guide plate 26 and the left light guide plate 28 are provided on the front frame 27. The right light guide plate 26 is situated in front of the right eye of the user when the user is wearing the image display unit 20, and allows the right eye to visually recognize an image. The left light guide plate 28 is situated in front of the left eye of the user when the user is wearing the image display unit 20, and allows the left eye to visually recognize an image.

The front frame 27 has a configuration that connects one end of the right light guide plate 26 and one end of the left light guide plate 28 to each other. The position of this connection corresponds to the position of the *glabella* of the user when the user is wearing the image display unit 20. On the front frame 27, a nose pad part to be butted against the nose of the user when the user is wearing the image display unit 20 may be provided at the connecting position between the right light guide plate 26 and the left light guide plate 28. In this case, the image display unit 20 can be held on the head of the user with the nose pad part, the right holding part 21, and the left holding part 23. Also, a belt that comes in contact with the back of the user's head when the user is wearing the image display unit 20 may be connected to the right holding part 21 and the left holding part 23. In this case, the image display unit 20 can be firmly held on the head of the user with the belt.

The right display unit 22 displays an image through the right light guide plate 26. The right display unit 22 is provided on the right holding part 21 and is situated near the right temporal region of the user when the user is wearing the image display unit 20. The left display unit 24 displays an image through the left light guide plate 28. The left display unit 24 is provided on the left holding part 23 and is situated near the left temporal region of the user when the user is wearing the image display unit 20. The right display unit 22 and the left display unit 24 are also collectively referred to as a "display drive unit".

The right light guide plate 26 and the left light guide plate 28 in this embodiment are optical units (for example, prisms) formed of a light-transmitting resin or the like, and guide image light outputted from the right display unit 22 and the left display unit 24 to the eyes of the user.

The image display unit 20 guides the image light generated by each of the right display unit 22 and the left display unit 24 to the right light guide plate 26 and the left light guide plate 28 and allows the user to visually recognize an image based on this image light (augmented reality (AR) image) (this is also referred to as "displaying an image").

A camera 61 is arranged on the front frame 27 of the image display unit 20. The camera 61 is provided at a position that does not block the external light transmitted through the right light guide plate 26 and the left light guide plate 28, on the front surface of the front frame 27. In the example of FIG. 1, the camera 61 is arranged on the side of the end part ER of the front frame 27. The camera 61 may be arranged on the side of the end part EL of the front frame 27, or may be arranged at the connecting part between the right light guide plate 26 and the left light guide plate 28.

The camera 61 is a digital camera having an image pickup element such as CCD or CMOS, and an image pickup lens or the like. While the camera 61 in this embodiment is a monocular camera, a stereo camera may be employed. The camera 61 picks up an image of at least a part of the external scenery (real space) in the direction of the front of the HMD 100, that is, in the field of vision visually recognized by the user when the user is wearing the image display unit 20. In other words, the camera 61 picks up an image in a range or direction overlapping with the field of vision of the user, and picks up an image in the direction in which the user looks. The width of the angle of view of the camera 61 can be suitably set. In this embodiment, the width of the angle of view of the camera 61 is set in such a way as to pick up an image of the entirety of the field of vision of the user that the user can visually recognize through the right light guide plate 26 and the left light guide plate 28. The camera 61 executes image pickup under the control of a control function unit 150 (FIG. 6), described later, and outputs the resulting external scenery picked-up image data to the control function unit 150.

Figure 2:
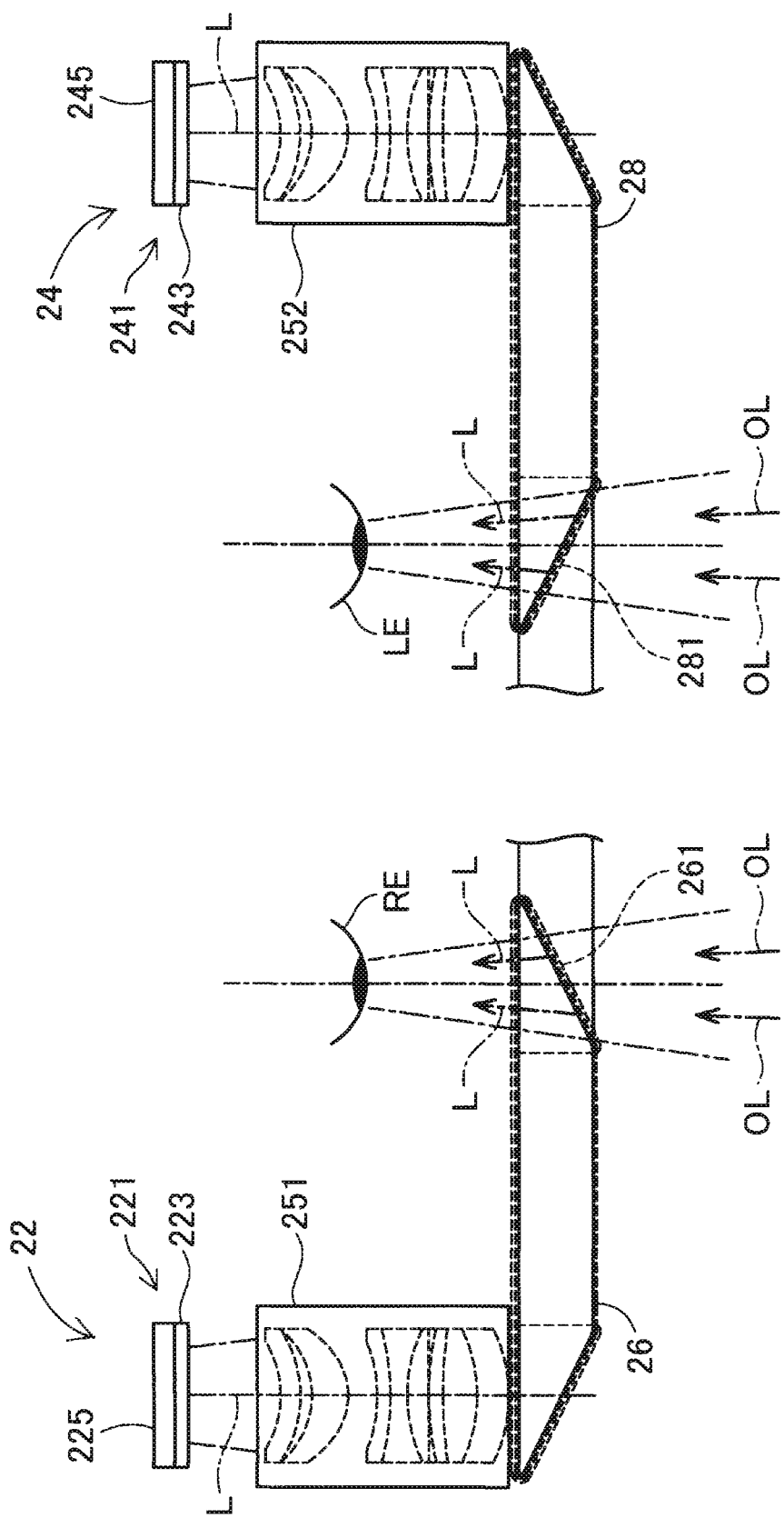
FIG. 2 is a plan view of essential parts showing the configuration of an optical system provided in an image display unit.

FIG. 2 is a plan view of essential parts showing the configuration of the optical system provided in the image display unit 20. For the sake of convenience of the description, FIG. 2 illustrates the right eye RE and the left eye LE of the user. As shown in FIG. 2, the right display unit 22 and the left display unit 24 are configured to be bilaterally symmetrical to each other.

As a configuration to allow the right eye RE to visually recognize an image (AR image), the right display unit 22 has an OLED (organic light emitting diode) unit 221 and a right optical system 251. The OLED unit 221 emits image light. The right optical system 251 has a lens group or the like and guides the image light L emitted from the OLED unit 221, to the right light guide plate 26.

The OLED unit 221 has an OLED panel 223 and an OLED drive circuit 225 which drives the OLED panel 223. The OLED panel 223 is a self-emitting display panel configured of light emitting elements which emit light by organic electroluminescence and emit color light of R (red), G (green), and B (blue), respectively. In the OLED panel 223, a plurality of pixels, each pixel including one R, G and B element each, is arranged in the form of a matrix.

Figure 5:
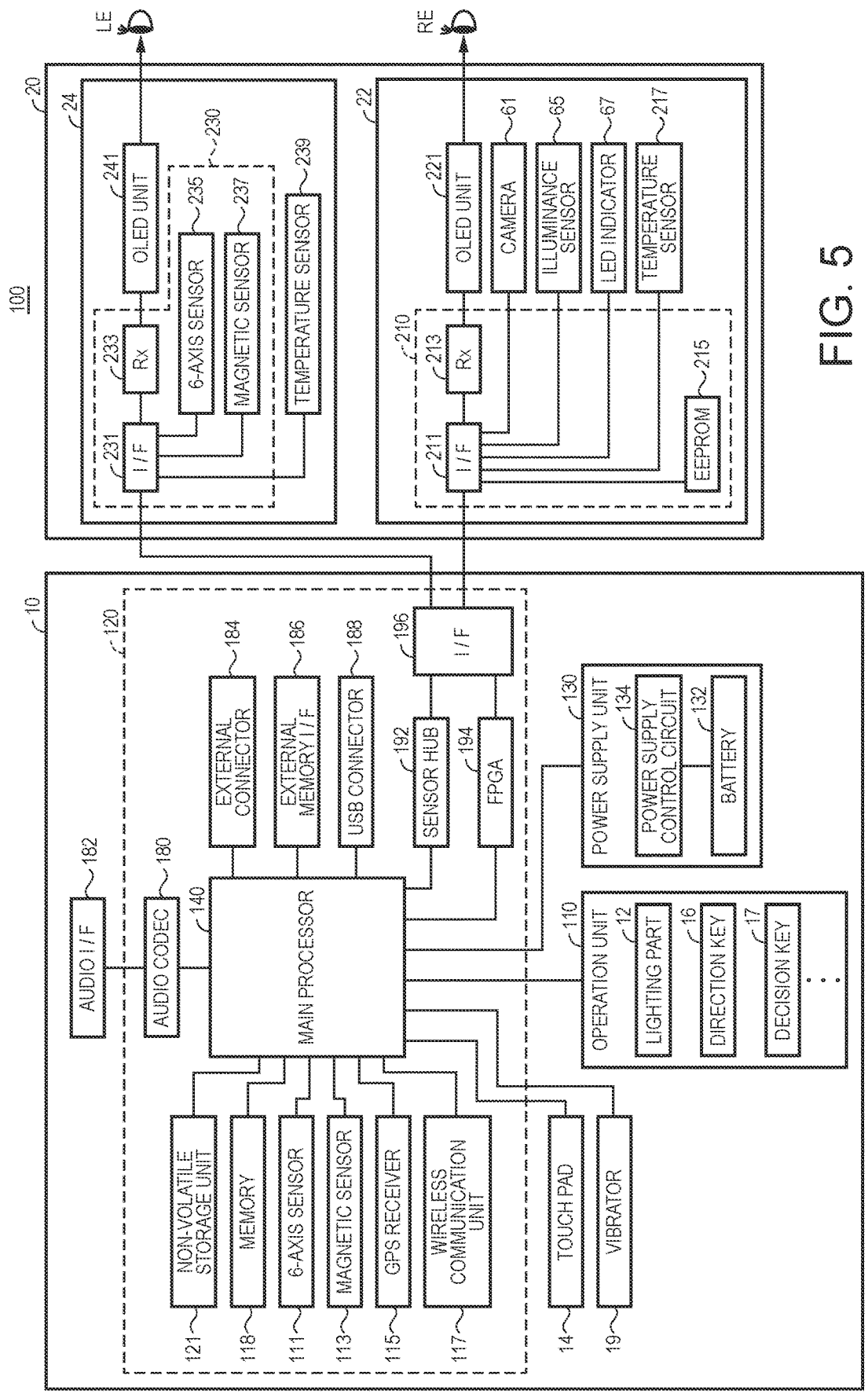
FIG. 5 is a block diagram functionally showing the configuration of an HMD.
Figure 6:
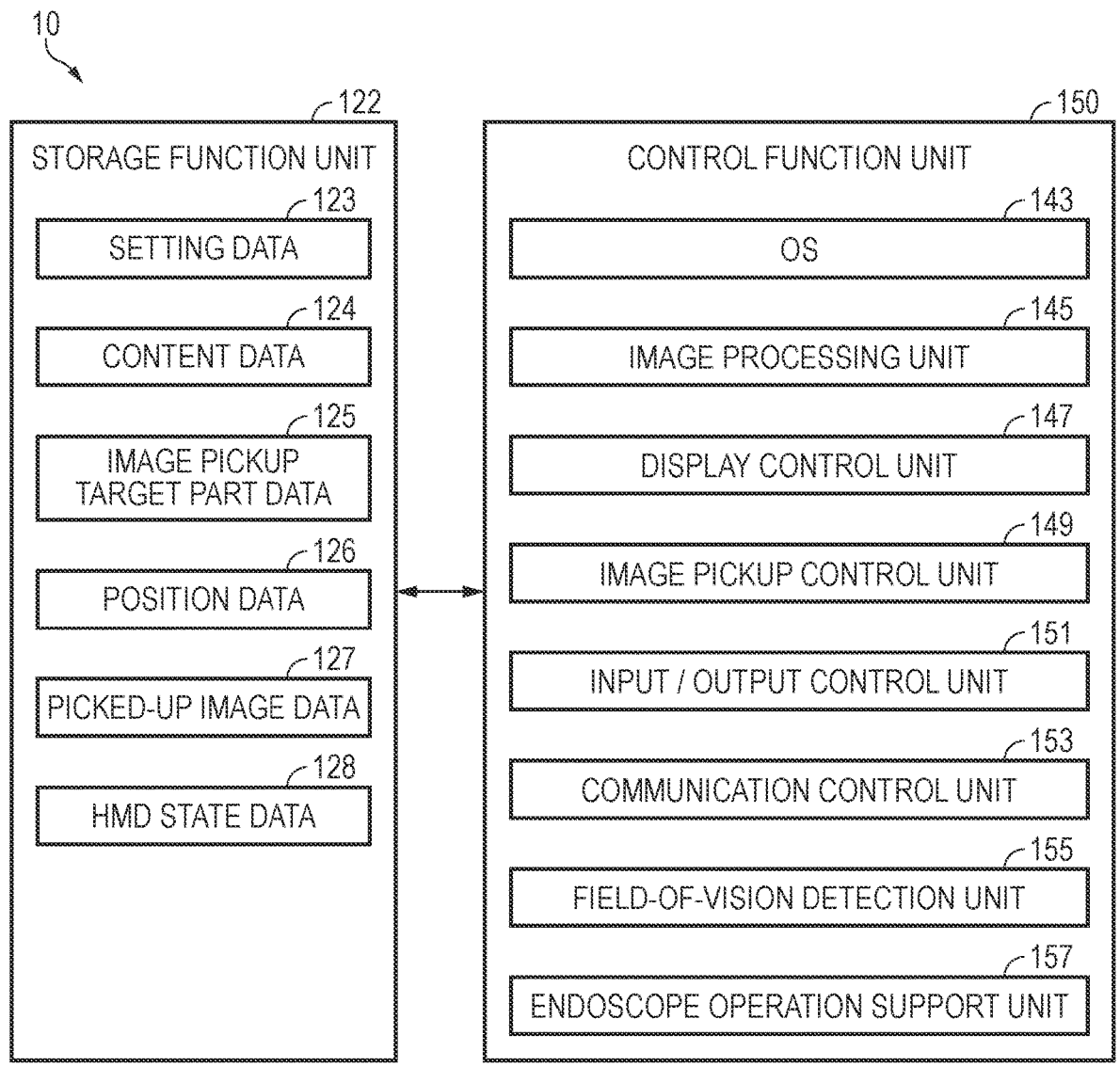
FIG. 6 is a block diagram functionally showing the configuration of a control device.

The OLED drive circuit 225 executes selection from and energization of the light emitting elements provided in the OLED panel 223 and causes the light emitting elements to emit light, under the control of the control function unit 150 (FIG. 6). The OLED drive circuit 225 is fixed to the backside of the OLED panel 223, that is, the back side of the light emitting surface, by bonding or the like. The OLED drive circuit 225 may be configured of, for example, a semiconductor device which drives the OLED panel 223, and may be mounted on a substrate fixed to the back side of the OLED panel 223. On this substrate, a temperature sensor 217 (FIG. 5), described later, is mounted. The OLED panel 223 may employ a configuration in which light emitting elements that emit white light are arranged in the form of a matrix, with color filters corresponding to the color light of R, G and B superimposed thereon. Moreover, the OLED panel 223 with a WRGB configuration having a light emitting element which radiates W (white) light in addition to light emitting elements which radiate the color light of R, G and B may be employed.

The right optical system 251 has a collimating lens which turns the image light L emitted from the OLED panel 223 into a parallel luminous flux. The image light L, turned into the parallel luminous flux by the collimating lens, becomes incident on the right light guide plate 26. In the optical path through which the light is guided inside the right light guide plate 26, a plurality of reflection surfaces that reflects the image light L is formed. The image light L is reflected a plurality of times inside the right light guide plate 26 and is thus guided toward the right eye RE. On the right light guide plate 26, a half mirror 261 (reflection surface) situated in front of the right eye RE is formed. The image light L is reflected by the half mirror 261 and subsequently emitted from the right light guide plate 26 to the right eye RE. This image light L forms an image on the retina of the right eye RE, thus allowing the user to visually recognize the image.

As a configuration to allow the left eye LE to visually recognize an image (AR image), the left display unit 24 has an OLED unit 241 and a left optical system 252. The OLED unit 241 emits image light. The left optical system 252 has a lens group or the like and guides the image light L emitted from the OLED unit 241, to the left light guide plate 28. The OLED unit 241 has an OLED panel 243 and an OLED drive circuit 245 which drives the OLED panel 243. The details of these respective parts are the same as those of the OLED unit 221, the OLED panel 223, and the OLED drive circuit 225. A temperature sensor 239 (FIG. 5), described later, is mounted on a substrate fixed to the back side of the OLED panel 243. The details of the left optical system 252 are the same as those of the right optical system 251.

With the configuration described above, the HMD 100 can function as a see-through display device. That is, the image light L reflected by the half mirror 261 and external light OL transmitted through the right light guide plate 26 become incident on the right eye RE of the user. The image light L reflected by a half mirror 281 and external light OL transmitted through the left light guide plate 28 become incident on the left eye LE of the user. In this way, the HMD 100 causes the image light L of the image processed inside and the external light OL to become incident, as superimposed on each other, on the eyes of the user. As a result, the user sees the external scenery (real world) through the right light guide plate 26 and the left light guide plate 28 and visually recognizes a virtual image (AR image) based on the image light L as superimposed on the external scenery.

The half mirror 261 and the half mirror 281 function as an "image extraction unit" which reflects the image light outputted from the right display unit 22 and the left display unit 24, respectively, and thus takes out an image. The right optical system 251 and the right light guide plate 26 are collectively referred to as a "right light guide unit". The left optical system 252 and the left light guide plate 28 are collectively referred to as a "left light guide unit". The configurations of the right light guide unit and the left light guide unit are not limited to the foregoing example. An arbitrary form can be used, provided that an image is formed in front of the eyes of the user, using image light. For the right light guide unit and the left light guide unit, for example, a diffraction grating may be used, or a semi-transmissive reflection film may be used.

In FIG. 1, the control device 10 and the image display unit 20 are connected together via a connection cable 40. The connection cable 40 is removably connected to a connector provided in a bottom part of the control device 10 and connects to various circuits inside the image display unit 20 from the distal end of the left holding part 23. The connection cable 40 has a metal cable or optical fiber cable which transmits digital data. The connection cable 40 may also include a metal cable which transmits analog data. A connector 46 is provided at a halfway point along the connection cable 40.

The connector 46 is a socket to connect a stereo mini plug. The connector 46 and the control device 10 are connected together, for example, via a line which transmits analog audio signals. In the example of this embodiment shown in FIG. 1, a headset 30 which includes a right earphone 32 and a left earphone 34 forming a stereo headphone and a microphone 63 is connected to the connector 46.

The microphone 63 is arranged in such a way that the sound collecting part of the microphone 63 faces the direction of the line of sight of the user, for example, as shown in FIG. 1. The microphone 63 collects sounds and outputs an audio signal to an audio interface 182 (FIG. 5). The microphone 63 may be a monaural microphone or stereo microphone, and may be a direction microphone or non-directional microphone.

The control device 10 is a device for controlling the HMD 100. The control device 10 includes a lighting part 12, a touch pad 14, a direction key 16, a decision key 17, and a power switch 18. The lighting part 12 notifies the operating state (for example, power ON/OFF or the like) of the HMD 100, by its light emitting mode. As the lighting part 12, for example, an LED (light emitting diode) can be used.

The touch pad 14 detects a touch operation on the operation screen of the touch pad 14 and outputs a signal corresponding to the detected content. As the touch pad 14, various touch pads such as electrostatic, pressure detection-type, and optical touch pads can be employed. The direction key 16 detects a press operation on keys corresponding to up, down, left and right directions and outputs a signal corresponding to the detected content. The decision key 17 detects a press operation and outputs a signal for deciding the content of the operation carried out on the control device 10. The power switch 18 switches the state of the power supply of the HMD 100 by detecting a slide operation of the switch.

Figure 3:
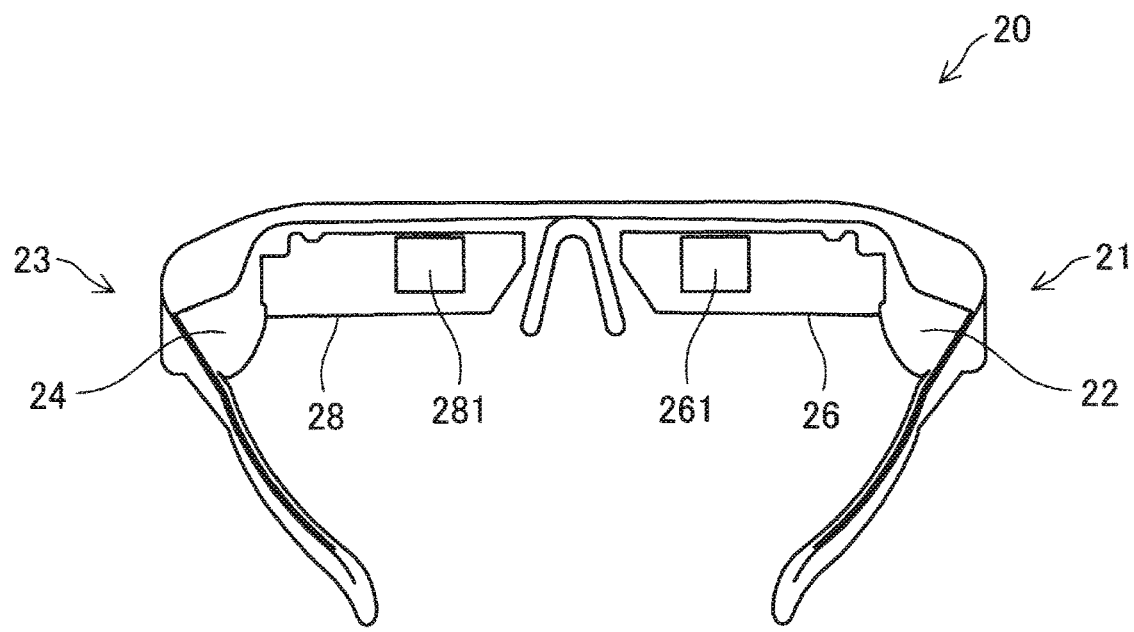
FIG. 3 shows the configuration of essential parts of the image display unit, as viewed from the user.

FIG. 3 shows the configuration of essential parts of the image display unit 20, as viewed from the user. In FIG. 3, the illustration of the connection cable 40, the right earphone 32, and the left earphone 34 is omitted. In the state shown in FIG. 3, the back sides of the right light guide plate 26 and the left light guide plate 28 can be visually recognized, and the half mirror 261 for casting image light to the right eye RE and the half mirror 281 for casting image light to the left eye LE can be visually recognized as substantially quadrilateral areas. The user visually recognizes the external scenery through the entirety of the left and right light guide plates 26, 28 including the half mirrors 261, 281, and also visually recognizes a rectangular display image at the positions of the half mirrors 261, 281.

Figure 4:
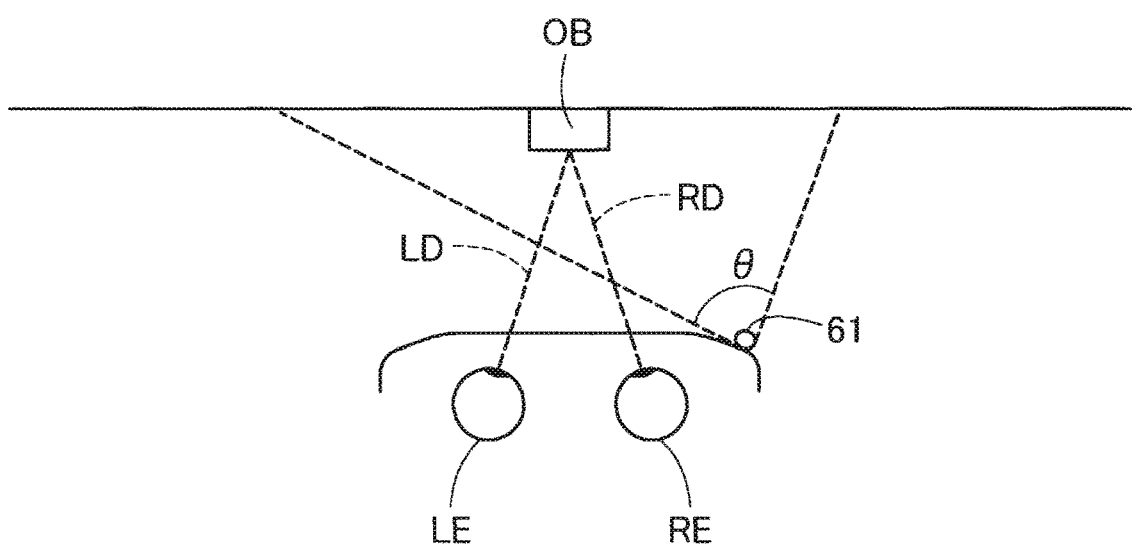
FIG. 4 explains the angle of view of a camera.

FIG. 4 explains the angle of view of the camera 61. In FIG. 4, the camera 61, and the right eye RE and the left eye LE of the user are schematically shown in a plan view, and the angle of view (image pickup range) of the camera 61 is indicated by θ. The angle of view θ of the camera 61 spreads in the horizontal direction as illustrated and also spreads in the vertical direction as with a general digital camera.

As described above, the camera 61 is arranged at the end part on the right-hand side of the image display unit 20, and picks up an image in the direction of the line of sight of the user (that is, in front of the user). Therefore, the optical axis of the camera 61 is in a direction including the directions of the lines of sight of the right eye RE and the left eye LE. The external scenery which the user can visually recognize when wearing the HMD 100 is not necessarily at infinity. For example, when the user gazes at an object OB with both eyes, the lines of sight of the user are directed to the object OB, as indicated by RD and LD in the illustration. In this case, the distance from the user to the object OB tends to be approximately 30 cm to 10 m, and more frequently, 1 m to 4 m. Thus, upper and lower limit benchmarks of the distance from the user to the object OB at the time of normal use may be defined for the HMD 100. The benchmarks may be found in advance and preset in the HMD 100, or may be set by the user. It is preferable that the optical axis and the angle of view of the camera 61 are set in such a way that the object OB is included in the angle of view when the distance to the object OB at the time of normal use corresponds to the set upper and lower limit benchmarks.

Generally, the human viewing angle is approximately 200 degrees horizontally and approximately 125 degrees vertically. Of this, the useful field of view, where an excellent information receptive ability can be exerted, is approximately 30 degrees horizontally and approximately 20 degrees vertically. The stable fixation field, where a gazing point at which a human gazes can be viewed quickly and stably, is approximately 60 to 90 degrees horizontally and approximately 45 to 70 degrees vertically. In this case, when the gazing point is the object OB (FIG. 4), the useful field of view is approximately 30 degrees horizontally and approximately 20 degrees vertically, with the lines of sight RD, LD at its center. The stable fixation field is approximately 60 to 90 degrees horizontally and approximately 45 to 70 degrees vertically. The actual field of view which the user visually recognizes through the image display unit 20 and through the right light guide plate 26 and the left light guide plate 28 is referred to as FOV (field of view). The field of view is narrower than the viewing angle and the stable fixation field but broader than the useful field of view. This field of view is equivalent to the "field of vision".

The angle of view θ of the camera 61 in this embodiment is set in such a way as to be able to pick up an image over a broader range than the field of view of the user. Preferably, the angle of view θ of the camera 61 may be set in such a way as to be able to pick up an image over at least a broader range than the useful field of view of the user. More preferably, the angle of view θ of the camera 61 may be set in such a way as to be able to pick up an image over a broader range than the field of view. More preferably, the angle of view θ of the camera 61 may be set in such a way as to be able to pick up an image over a broader range than the stable fixation field of the user. Most preferably, the angle of view θ of the camera 61 may be set in such a way as to be able to pick up an image over a broader range than the viewing angles of both eyes of the user. Therefore, the camera 61 may have a so-called wide-angle lens as an image pickup lens and thus may be configured to be able to pick up an image over a broad angle of view. The wide-angle lens may include a lens called an ultra-wide-angle lens or quasi-wide-angle lens. The camera 61 may also include a monofocal lens or a zoom lens, and may include a lens group made up of a plurality of lenses.

FIG. 5 is a block diagram functionally showing the configuration of the HMD 100. The control device 10 includes a main processor 140 which executes a program and controls the HMD 100, a storage unit, an input/output unit, sensors, an interface, and a power supply unit 130. The storage unit, the input/output unit, the sensors, the interface, and the power supply unit 130 are connected to the main processor 140. The main processor 140 is mounted on a controller board 120 built in the control device 10.

The storage unit includes a memory 118 and a non-volatile storage unit 121. The memory 118 forms a work area for temporarily storing a computer program executed by the main processor 140 and data processed by the main processor 140. The non-volatile storage unit 121 is configured of a flash memory or eMMC (embedded multimedia card). The non-volatile storage unit 121 stores a computer program executed by the main processor 140 and various data processed by the main processor 140. In this embodiment, these storage units are mounted on the controller board 120.

The input/output unit includes the touch pad 14 and an operation unit 110. The operation unit 110 includes the direction key 16, the decision key 17, and the power switch 18 provided in the control device 10. The main processor 140 controls each of these input/output units and acquires a signal outputted from each of the input/output units.

The sensors include a 6-axis sensor 111, a magnetic sensor 113, and a GPS (global positioning system) receiver 115. The 6-axis sensor 111 is a motion sensor (inertial sensor) having a 3-axis acceleration sensor and a 3-axis gyro (angular velocity) sensor. As the 6-axis sensor 111, an IMU (inertial measurement unit) in which these sensors are formed as modules may be employed. The magnetic sensor 113 is, for example, a 3-axis geomagnetic sensor. The GPS receiver 115 has a GPS antenna, not illustrated, and thus receives radio signals transmitted from GPS satellites and detects the coordinates of the current location of the control device 10. These sensors (6-axis sensor 111, magnetic sensor 113, GPS receiver 115) output detected values to the main processor 140 according to a sampling frequency designated in advance. The timing when each sensor outputs a detected value may be in response to an instruction from the main processor 140.

The interface includes a wireless communication unit 117, an audio codec 180, an external connector 184, an external memory interface 186, a USB (universal serial bus) connector 188, a sensor hub 192, an FPGA 194, and an interface 196. These components function as interfaces to the outside. The wireless communication unit 117 executes wireless communication between the HMD 100 and an external device. The wireless communication unit 117 includes an antenna, an RF circuit, a baseband circuit, a communication control circuit and the like, not illustrated. Alternatively, the wireless communication unit 117 is configured as a device in which these components are integrated. The wireless communication unit 117 carries out wireless communication conforming to a wireless LAN standard including, for example, Bluetooth (trademark registered) or Wi-Fi (trademark registered).

The audio codec 180 is connected to an audio interface 182 and encodes or decodes an audio signal inputted or outputted via the audio interface 182. The audio interface 182 is an interface for inputting or outputting an audio signal. The audio codec 180 may have an A/D converter which converts an analog audio signal into digital audio data, or a D/A converter which carries out reverse conversion. The HMD 100 in this embodiment outputs a sound from the right earphone 32 and the left earphone 34 and collects a sound with the microphone 63. The audio codec 180 converts digital audio data outputted from the main processor 140 into an analog audio signal and outputs the analog audio signal via the audio interface 182. Also, the audio codec 180 converts an analog audio signal inputted to the audio interface 182 into digital audio data and outputs the digital audio data to the main processor 140.

The external connector 184 is a connector for connecting, to the main processor 140, an external device (for example, a personal computer, smartphone, game machine or the like) which communicates with the main processor 140. The external device connected to the external connector 184 can be a source of a content and can also be used to debug a computer program executed by the main processor 140 or to collect operation logs of the HMD 100. The external connector 184 can employ various forms. As the external connector 184, for example, an interface supporting wired connection such as a USB interface, micro USB interface or memory card interface, or an interface supporting wireless connection such as a wireless LAN interface or Bluetooth interface can be employed.

The external memory interface 186 is an interface to which a portable memory device can be connected. The external memory interface 186 includes, for example, a memory card slot in which a card-type recording medium is loaded to read or write data, and an interface circuit. The size, shape, standard and the like of the card-type recording medium can be suitably selected. The USB connector 188 is an interface to which a memory device, smartphone, personal computer or the like conforming to the USB standard can be connected. The USB connector 188 includes, for example, a connector conforming to the USB standard, and an interface circuit. The size, shape, USB standard version and the like of the USB connector 188 can be suitably selected.

The HMD 100 also has a vibrator 19. The vibrator 19 has a motor and an eccentric rotor or the like, not illustrated, and generates vibration under the control of the main processor 140. For example, when an operation on the operation unit 110 is detected or when the power of the HMD 100 is switched on/off, or the like, the HMD 100 causes the vibrator 19 to generate vibration in a predetermined vibration pattern. The vibrator 19 may be provided on the side of the image display unit 20, for example, in the right holding part 21 (right temple part) of the image display unit, instead of being provided in the control device 10.

The sensor hub 192 and the FPGA 194 are connected to the image display unit 20 via the interface (I/F) 196. The sensor hub 192 acquires detected values from various sensors provided in the image display unit 20 and outputs the detected values to the main processor 140. The FPGA 194 executes processing of data sent and received between the main processor 140 and each part of the image display unit 20 and transmission of the data via the interface 196. The interface 196 is connected to each of the right display unit 22 and the left display unit 24 of the image display unit 20. In the example of this embodiment, the connection cable 40 is connected to the left holding part 23, and a wire leading to this connection cable 40 is laid inside the image display unit 20. Each of the right display unit 22 and the left display unit 24 is connected to the interface 196 of the control device 10.

The power supply unit 130 includes a battery 132 and a power supply control circuit 134. The power supply unit 130 supplies electric power for the control device 10 to operate. The battery 132 is a rechargeable battery. The power supply control circuit 134 detects the remaining capacity of the battery 132 and controls the recharging of the battery 132. The power supply control circuit 134 is connected to the main processor 140 and outputs the detected value of the remaining capacity of the battery 132 and the detected value of the voltage of the battery 132 to the main processor 140. Based on the electric power supplied by the power supply unit 130, electric power may be supplied from the control device 10 to the image display unit 20. The main processor 140 may be configured to be able to control the state of supply of electric power from the power supply unit 130 to each part of the control device 10 and the image display unit 20.

The right display unit 22 has a display unit board 210, the OLED unit 221, the camera 61, an illuminance sensor 65, an LED indicator 67, and a temperature sensor 217. On the display unit board 210, an interface (I/F) 211 connected to the interface 196, a receiving unit (Rx) 213, and an EEPROM (electrically erasable programmable read-only memory) 215 are mounted. The receiving unit 213 receives data inputted from the control device 10 via the interface 211. When image data of an image to be displayed by the OLED unit 221 is received, the receiving unit 213 outputs the received image data to the OLED drive circuit 225 (FIG. 2).

The EEPROM 215 stores various data in a form readable by the main processor 140. The EEPROM 215 stores, for example, data about light emission characteristics and display characteristics of the OLED units 221, 241 of the image display unit 20, and data about sensor characteristics of the right display unit 22 and the left display unit 24, or the like. Specifically, the EEPROM 215 stores, for example, a parameter for gamma correction of the OLED units 221, 241, and data for compensating for detected values from the temperature sensors 217, 239, or the like. These data are generated by an inspection and written in the EEPROM 215 at the time of shipping the HMD 100 from the plant. After the shipping, the main processor 140 reads the data in the EEPROM 215 and uses the data for various kinds of processing.

The camera 61 executes image pickup according to a signal inputted via the interface 211 and outputs picked-up image data or a signal indicating the result of the image pickup to the control device 10. The illuminance sensor 65 is provided at the end part ER of the front frame 27 and arranged in such a way as to receive external light from the front of the user wearing the image display unit 20, as shown in FIG. 1. The illuminance sensor 65 outputs a detected value corresponding to the amount of light received (intensity of received light). The LED indicator 67 is arranged near the camera 61 at the end part ER of the front frame 27, as shown in FIG. 1. The LED indicator 67 turns on during the execution of image pickup by the camera 61 and thus reports that image pickup is in progress.

The temperature sensor 217 detects temperature and outputs a voltage value or resistance value corresponding to the detected temperature. The temperature sensor 217 is mounted on the back side of the OLED panel 223 (FIG. 3). The temperature sensor 217 may be mounted, for example, on the same substrate as the OLED drive circuit 225. With this configuration, the temperature sensor 217 mainly detects the temperature of the OLED panel 223. Also, the temperature sensor 217 may be built in the OLED panel 223 or the OLED drive circuit 225. For example, if the OLED panel 223 as a Si-OLED is mounted along with the OLED drive circuit 225 as an integrated circuit on an integrated semiconductor chip, the temperature sensor 217 may be mounted on this semiconductor chip.

The left display unit 24 has a display unit board 230, the OLED unit 241, and a temperature sensor 239. On the display unit board 230, an interface (I/F) 231 connected to the interface 196, a receiving unit (Rx) 233, a 6-axis sensor 235, and a magnetic sensor 237 are mounted. The receiving unit 233 receives data inputted from the control device 10 via the interface 231. When image data of an image to be displayed by the OLED unit 241 is received, the receiving unit 233 outputs the received image data to the OLED drive circuit 245 (FIG. 2).

The 6-axis sensor 235 is a motion sensor (inertial sensor) having a 3-axis acceleration sensor and a 3-axis gyro (angular velocity) sensor. As the 6-axis sensor 235, an IMU sensor in which the above sensors are formed as modules may be employed. The magnetic sensor 237 is, for example, a 3-axis geomagnetic sensor. The 6-axis sensor 235 and the magnetic sensor 237 are provided in the image display unit 20 and therefore detect a movement of the head of the user when the image display unit 20 is mounted on the head of the user. Based on the detected movement of the head, the direction of the image display unit 20 is specified and the field of vision of the user is specified. Based on the result of the image pickup by the camera 61, the area of external scenery visually recognized in the specified field of vision of the user is specified.

The temperature sensor 239 detects temperature and outputs a voltage value or resistance value corresponding to the detected temperature. The temperature sensor 239 is mounted on the back side of the OLED panel 243 (FIG. 3). The temperature sensor 239 may be mounted, for example, on the same substrate as the OLED drive circuit 245. With this configuration, the temperature sensor 239 mainly detects the temperature of the OLED panel 243. The temperature sensor 239 may be built in the OLED panel 243 or the OLED drive circuit 245. The details of the temperature sensor 239 are similar to those of the temperature sensor 217.

The camera 61, the illuminance sensor 65 and the temperature sensor 217 of the right display unit 22, and the 6-axis sensor 235, the magnetic sensor 237 and the temperature sensor 239 of the left display unit 24 are connected to the sensor hub 192 of the control device 10. The sensor hub 192 carries out setting of a sampling frequency and initialization of each sensor under the control of the main processor 140. The sensor hub 192 executes energization of each sensor, transmission of control data, acquisition of a detected value or the like, according to the sampling period of each sensor. The sensor hub 192 outputs the detected value from each sensor provided in the right display unit 22 and the left display unit 24 to the main processor 140 at a preset timing. The sensor hub 192 may have a cache function to temporarily hold the detected value from each sensor. The sensor hub 192 may have a signal format or data format conversion function (for example, to convert to a unified format) for the detected value from each sensor. The FPGA 194 starts or stops the energization of the LED indicator 67 under the control of the main processor 140 and thus causes the LED indicator 67 to turn on or off.

FIG. 6 is a block diagram functionally showing the configuration of the control device 10. Functionally, the control device 10 has a storage function unit 122 and a control function unit 150. The storage function unit 122 is a logical storage unit configured of the non-volatile storage unit 121 (FIG. 5). The storage function unit 122 may have a configuration using the EEPROM 215 and the memory 118 in combination with the non-volatile storage unit 121, instead of the configuration using only the non-voltage storage unit 121. The control function unit 150 is configured by the main processor 140 executing a computer program, that is, by hardware and software collaborating with each other. The control function unit 150 is equivalent to the "control unit" according to the invention.

In the storage function unit 122, various data used for processing in the control function unit 150 are stored. Specifically, in the storage function unit 122 in this embodiment, setting data 123, content data 124, image pickup target part data 125, position data 126, picked-up image data 127, and HMD state data 128 are stored. The setting data 123 includes various setting values related to the operation of the HMD 100. For example, the setting data 123 includes a parameter, determinant, arithmetic expression, LUT (lookup table) or the like used when the control function unit 150 controls the HMD 100.

The content data 124 includes data of a content (image data, video data, audio data or the like) including an image or video to be displayed by the image display unit 20 under the control of the control function unit 150. For example, the content data 124 includes a pointer image data or direction image data displayed for the support of endoscope operation, described later. The content data 124 may include data of a bidirectional content. The bidirectional content refers to a content of such a type that an operation by the user is acquired via the operation unit 110, then processing corresponding to the content of the acquired operation is executed by the control function unit 150, and a content corresponding to the content of the processing is displayed by the image display unit 20. In this case, the data of the content can include image data of a menu screen for acquiring the operation by the user, and data for deciding processing corresponding to an item included in the menu screen, and the like.

The image pickup target part data 125 include data expressing a target part to be inspected (hereinafter also referred to as an "image pickup target part") in the form of a two-dimensional (2D) or three-dimensional (3D) structure, and data of the appearance (entirety or feature points) of an object including the image pickup target part. In this embodiment, the tubular organs from the oral cavity to the anus of the subject TS (in FIG. 1, the oral cavity to the stomach are indicated by dashed lines) are then image pickup target part IT. The position data 126 includes data indicating the position of the distal end part 340, as the position where image pickup is carried out with the endoscope unit 310 of the endoscope device 300. The picked-up image data 127 includes image data picked up at the current position (also referred to as "endoscope picked-up image data"). The image pickup target part data 125, the position data 126, and the picked-up image data (endoscope picked-up image data) 127 are transmitted from the endoscope control device 400 via wireless communication and stored in the storage function unit 122, as will be described later. As the picked-up image data 127 and the position data 126, endoscope picked-up image data picked up by the image pickup unit 342 on a predetermined frame cycle, and data indicating the position of the distal end part 340 at the time of image pickup are sequentially received. As the HMD state data 128, the field of vision of the user is specified by a field-of-vision detection unit 155, described later, and data of the specified field of vision is stored.

The control function unit 150 executes various kinds of processing using the data stored in the storage function unit 122, and thus executes the functions of an OS 143, an image processing unit 145, a display control unit 147, an image pickup control unit 149, an input/output control unit 151, a communication control unit 153, a field-of-vision detection unit 155, and an endoscope operation support unit 157. In this embodiment, each of the functional units other than the OS 143 is configured as a computer program executed on the OS 143.

The image processing unit 145 generates a signal to be transmitted to the right display unit 22 and the left display unit 24, based on image data of an image or video to be displayed by the image display unit 20. The signal generated by the image processing unit 145 may be a vertical synchronization signal, horizontal synchronization signal, clock signal, analog image signal or the like. The image processing unit 145 may be realized by the main processor 140 (FIG. 5) executing a computer program, or may be configured of hardware (for example, DSP (digital signal processor)) other than the main processor 140.

The image processing unit 145 may execute resolution conversion processing, image adjustment processing, 2D/3D conversion processing or the like, according to need. The resolution conversion processing is processing to convert the resolution of image data to a resolution suitable for the right display unit 22 and the left display unit 24. The image adjustment processing is processing to adjust the luminance and saturation of image data. The 2D/3D conversion processing is processing to generate two-dimensional image data from three-dimensional image data, or to generate three-dimensional image data from two-dimensional image data. In the case where such processing is executed, the image processing unit 145 generates a signal for displaying an image based on the image data resulting from the processing, and transmits the signal to the image display unit 20 via the connection cable 40 (FIG. 1).

The display control unit 147 generates a control signal to control the right display unit 22 and the left display unit 24, and with this control signal, controls the generation and emission of image light by each of the right display unit 22 and the left display unit 24. Specifically, the display control unit 147 controls the OLED drive circuits 225, 245 so as to cause the OLED panels 223, 243 to display an image. Based on a signal outputted from the image processing unit 145, the display control unit 147 performs control on the timing when the OLED drive circuits 225, 245 cause the OLED panels 223, 243 to display an image, and control on the luminance of the OLED panels 223, 243, or the like.

The image pickup control unit 149 controls the camera 61 (FIG. 5) to execute image pickup, generate external scenery picked-up image data, and store the external scenery picked-up image data temporarily in the storage function unit 122. If the camera 61 is configured as a camera unit including a circuit which generates external scenery picked-up image data, the image pickup control unit 149 acquires external scenery picked-up image data from the camera 61 and stores the external scenery picked-up image data temporarily in the storage function unit 122.

The input/output control unit 151 controls the touch pad 14 (FIG. 1), the direction key 16, and the decision key 17 appropriately, and acquires an input command from these. The acquired command is outputted to the OS 143 or a computer program operating on the OS 143 along with the OS 143. The communication control unit 153 controls the wireless communication unit 117 to carry out wireless communication with the endoscope control device 400.

The field-of-vision detection unit 155 specifies the field of vision of the user, based on the direction of the image display unit 20 specified from the movement of the head detected at any time by the 6-axis sensor 235 and the magnetic sensor 237, and the image data picked up by the camera 61, and stores data of the specified field of vision as included in the HMD state data 128.

The endoscope operation support unit 157 acquires image pickup target part data, position data, and picked-up image data from the endoscope control device 400 (FIG. 1), and causes the image display unit 20 to display a position display image showing the current position where image pickup is being carried out by the endoscope unit 310 and a picked-up image taken at the current position, as images for supporting the operation of the endoscope unit 310 (FIG. 1), as will be described later.

Figure 7:
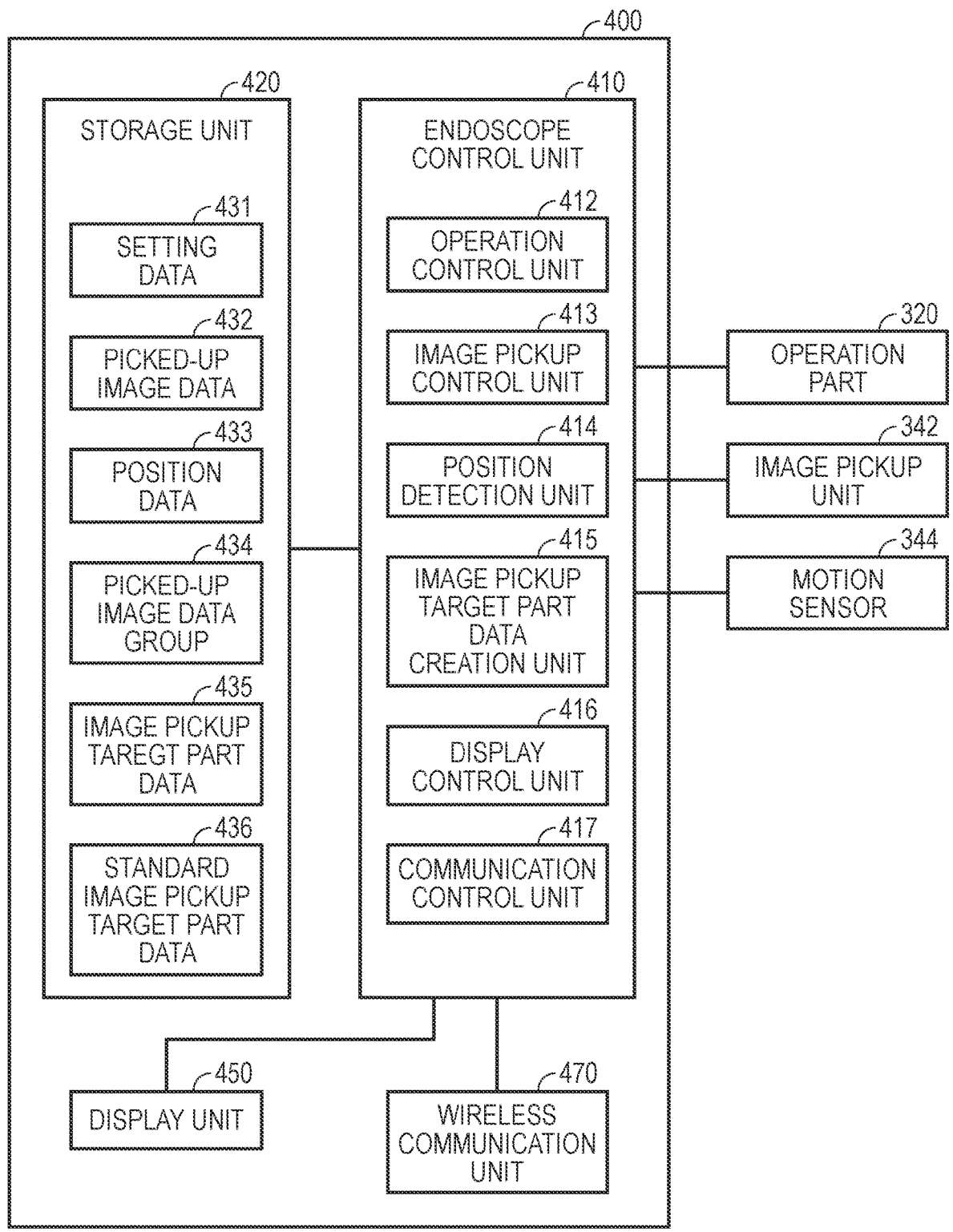
FIG. 7 is a block diagram functionally showing the configuration of an endoscope control device.

FIG. 7 is a block diagram functionally showing the configuration of the endoscope control device 400. The endoscope control device 400 includes an endoscope control unit 410, a storage unit 420, a display unit 450, a wireless communication unit 470, and a light source generation unit, not illustrated. In the endoscope control device 400, each of the storage unit 420, the display unit 450, the wireless communication unit 470, and the light source generation unit is connected to the endoscope control unit 410. Also, the operation part 320 of the endoscope unit 310 (FIG. 1), the image pickup unit 342 provided at the distal end part 340 of the insertion part 330, and a motion sensor 344 are connected to the endoscope control unit 410 via the connection part 350. Moreover, the illumination lens is connected to the light source generation unit via the optical fiber inside the connection part 350. As the motion sensor 344, an acceleration sensor for three axial directions, an angular velocity sensor for three axial directions, or the like is used. In this embodiment, a 6-axis sensor capable of calculating the direction of movement, direction, rotation, moving distance, and moving speed, by a combination of an acceleration sensor for three axial directions and an angular velocity sensor for three axial directions, is used.

The endoscope control unit 410 is a computer and functions as various control units by executing a computer program stored in a memory, not illustrated. In FIG. 7, an operation control unit 412, an image pickup control unit 413, a position detection unit 414, an image pickup target part data creation unit 415, a display control unit 416, and a communication control unit 417 are shown.

The operation control unit 412 is a function control unit which controls basic operations of the endoscope unit 310 corresponding to operations by the user supplied from the operation part 320. The image pickup control unit 413 is a function control unit which controls the illumination operation of the light source generation unit and the image pickup operation of the image pickup unit 342. The image pickup unit 342 executes the image pickup operation on a predetermined frame cycle under the control of the image pickup control unit 413. The image data picked up by the image pickup unit 342 is successively stored in the storage unit 420 as picked-up image data 432. The position detection unit 414 is a function control unit which detects the current position of the distal end part 340, based on the movement of the distal end part 340 detected by the motion sensor 344, as will be described later. The information of the detected movement and current position of the distal end part 340 is stored in the storage unit 420 as position data 433. The picked-up image data 432 and the position data 433 successively stored in the storage unit 420 are successively transmitted to the control device 10 via the communication control unit 417 and the wireless communication unit 470 by the operation control unit 412.

The image pickup target part data creation unit 415 is a function control unit which accumulates the picked-up image data 432 obtained on the frame cycle in the storage unit 420 as a picked-up image data group 434 and creates structure data expressing the structure of the image pickup target part, using the picked-up image data group 434, as will be described later. The structure data of the image pickup target part thus created is stored in the storage unit 420 as image pickup target part data 435.

The display control unit 416 is a function control unit which controls the display operation of the picked-up image picked up by the image pickup unit 342 or an operation menu screen or the like, on the display unit 450 including a display device, not illustrated. The communication control unit 417 carries out wireless communication with the control device 10 of the HMD 100 via the wireless communication unit 470. The wireless communication unit 470 carries out wireless communication, for example, conforming to a wireless LAN standard including Bluetooth (trademark registered) or Wi-Fi (trademark registered).

In the storage unit 420, the picked-up image data 432, the position data 433, the picked-up image data group 434, the image pickup target part data 435, and standard image pickup target part data 436 expressing a standard structure of the image pickup target part IT (FIG. 1) are stored, and basic setting data 431 for the operations of the respective units 412 to 417 is stored as well.

A2. Endoscope Operation Support Processing

Hereinafter, first, image pickup/position detection processing and image pickup target part data creation processing executed in the endoscope control device 400 will be described, and then, endoscope operation support processing in the HMD 100 will be described.

Figure 8:
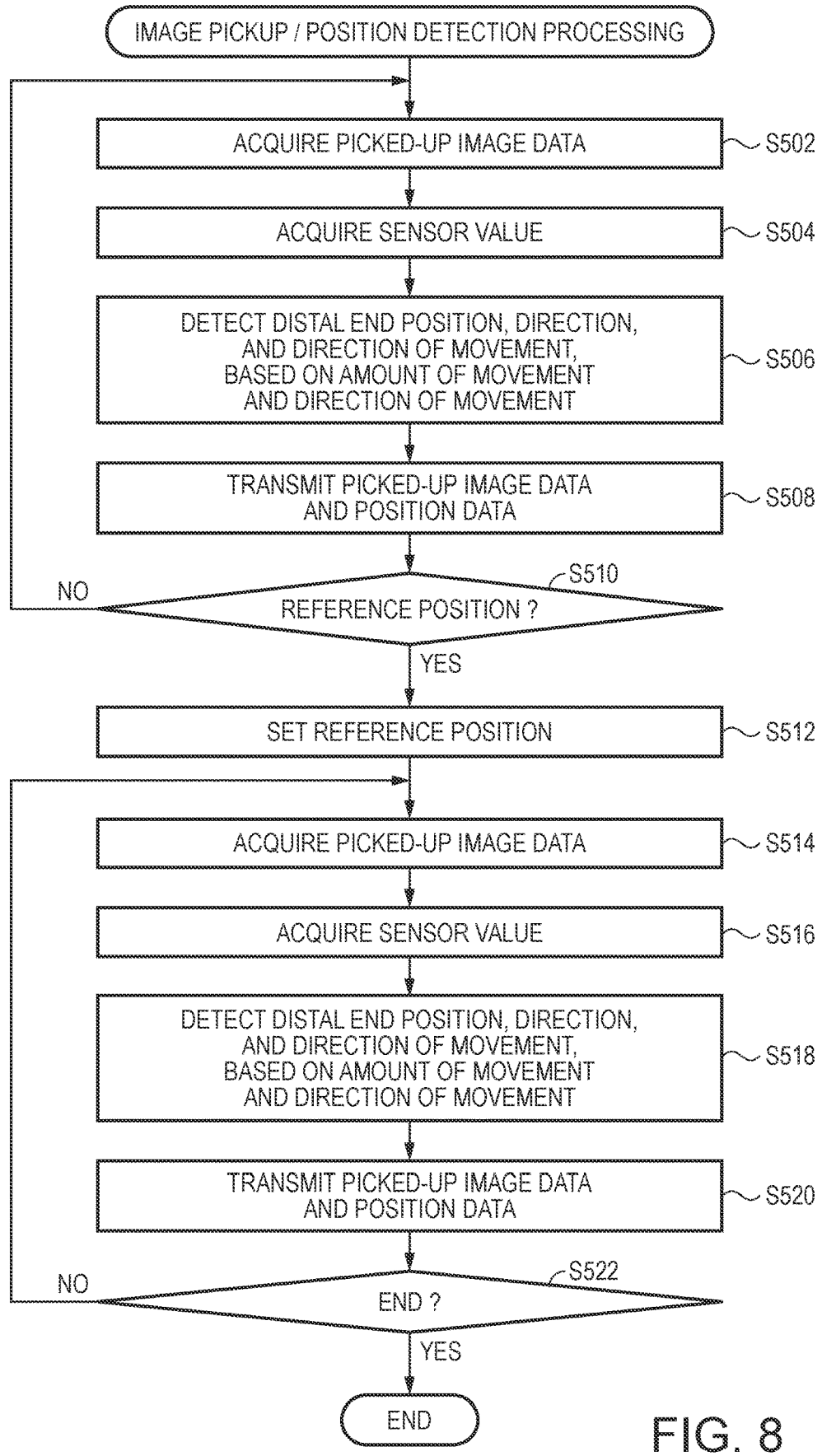
FIG. 8 is a flowchart showing image pickup/position detection processing executed in the endoscope control device.

FIG. 8 is a flowchart showing the image pickup/position detection processing executed in the endoscope control device 400. This processing is executed repeatedly on a predetermined frame cycle by the operation control unit 412 collaborating with the image pickup control unit 413 and the position detection unit 414 after the endoscope device 300 is started up, until an instruction to end the processing is given. First, in Step S502, the image pickup control unit 413 causes the image pickup unit 342 to pick up an image, and picked-up image data expressing the picked-up image is acquired and stored in the storage unit 420 as the picked-up image data 432. In Step S504, a sensor value outputted from the motion sensor 344 at the position where the image pickup in Step S502 is carried out is acquired by the position detection unit 414. In Step S506, the current position (distal end position) of the distal end part 340 where image pickup is carried out, the direction of the distal end part 340 (direction of the distal end surface facing the image pickup unit 342), and the direction of movement of the distal end part 340 are detected by the position detection unit 414 and stored in the storage unit 420 as the position data 433. Specifically, based on the data of the position (previous distal end position) of the distal end part 340 before the acquisition of the sensor value, and the acquired sensor value, the amount of movement and the direction of movement of the distal end part 340 are found. Then, based on the previous distal end position, and the amount of movement and the direction of movement thus found, the current position of the distal end part 340 (current distal end position), the direction of the distal end part 340, and the direction of movement of the distal end part 340 are detected. In Step S508, the picked-up image data 432 and the position data 433 are transmitted to the control device 10 by the operation control unit 412 via the communication control unit 417 and the wireless communication unit 470.

Next, in Step S510, the position detection unit 414 determines whether the detected distal end position is a reference position or not. This can be determined, for example, based on whether the picked-up image expressed by the picked-up image data 432 coincides with a feature image corresponding to a predetermined feature part (for example, the pharynx, larynx or the like) inside the image pickup target part IT or not. The image data of the feature image is included in the standard image pickup target part data 436. The coincidence with the feature image is not perfect coincidence and may include the case where the degree of coincidence between a feature part candidate image extracted from the picked-up image expressed by the picked-up image data 432 and a feature image in the image expressed by the standard image pickup target part data 436 is equal to or higher than a predetermined degree of accuracy.

If it is determined that the detected distal end position is not the reference position, the processing of Steps S502 to S508 is repeated. Meanwhile, if it is determined that the detected distal end position is the reference position, the position data of the distal end position in the position data 433 is set as position data of a predetermined reference position (Step S512), and the subsequent processing is executed, based on this position as a reference.

In Step S514, as in Step S502, picked-up image data is acquired by the image pickup control unit 413 and stored in the storage unit 420 as the picked-up image data 432. In Step S516, as in Step S504, a sensor value is acquired by the position detection unit 414. In Step S518, as in Step S506, the position of the distal end part 340 (distal end position), the direction of the distal end surface of the distal end part 340 facing the image pickup unit 342 (direction of the distal end part), and the direction of movement of the distal end part 340 are detected by the position detection unit 414 and stored in the storage unit 420 as the position data 433. In Step S520, as in Step S508, the picked-up image data 432 and the position data 433 stored in the storage unit 420 are transmitted to the control device 10 by the operation control unit 412 via the communication control unit 417 and the wireless communication unit 470. Then, the processing of image pickup/position detection in Steps S514 to S520 is executed repeatedly until an instruction to end the processing is given by an end sequence.

As described above, in the endoscope control device 400, after the endoscope device 300 is started up, the image pickup/position detection processing is executed by the operation control unit 412 collaborating with the image pickup control unit 413 and the position detection unit 414, until an instruction to end the processing is given. This processing may be started not only automatically after the startup of the endoscope device 300 but may also be started by an instruction based on a start button or a sound or the like after the startup of the endoscope device 300. This processing may be started by generating various start triggers. The same applies to the ending of the processing.

Figure 9:
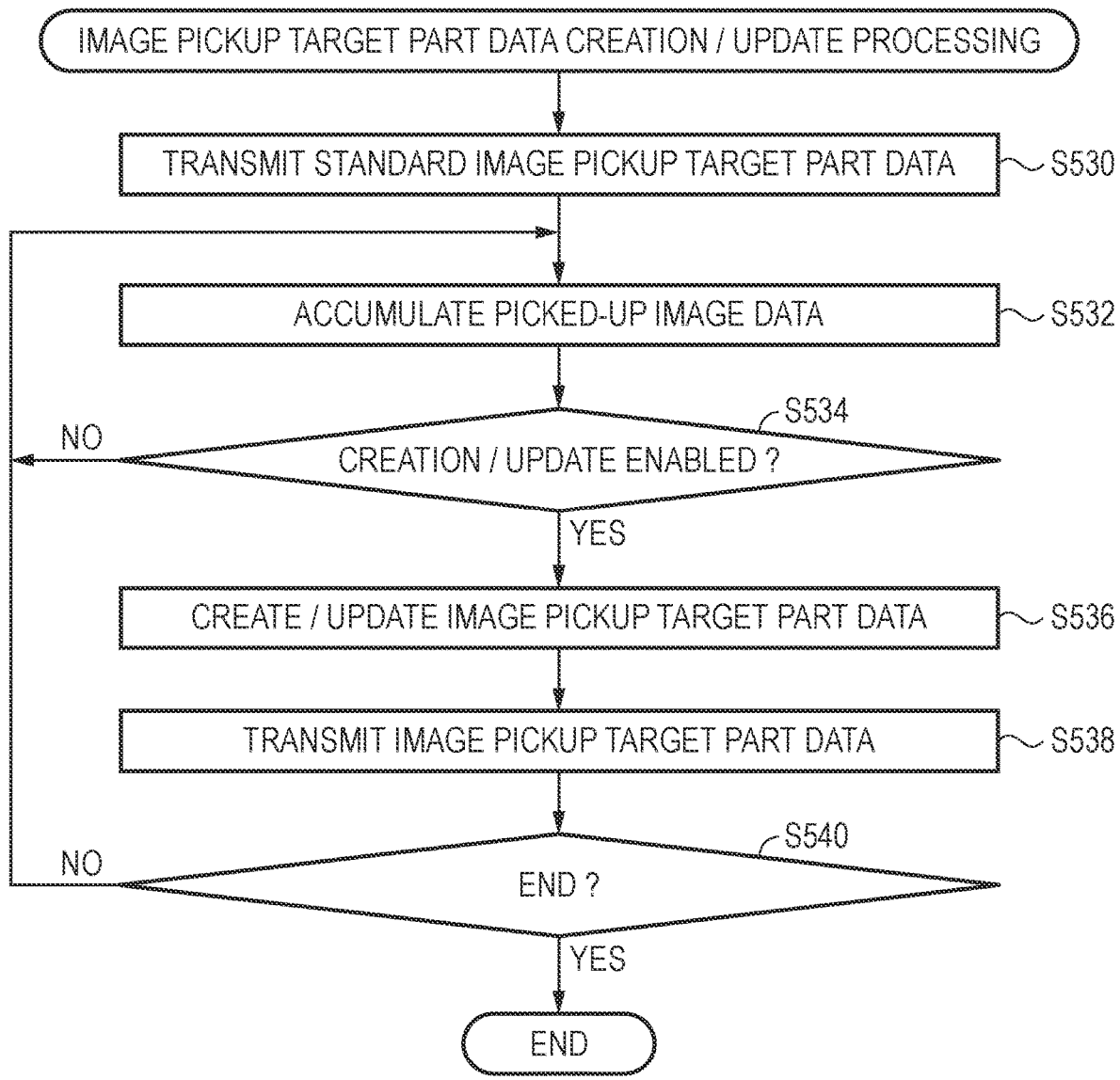
FIG. 9 is a flowchart showing image pickup target part data creation processing executed in the endoscope control device.

FIG. 9 is a flowchart showing the image pickup target part data creation processing executed in the endoscope control device 400. Similarly to the image pickup/position detection processing (FIG. 8), this processing, too, is executed by the operation control unit 412 collaborating with the image pickup target part data creation unit 415 after the endoscope device 300 is started up, until an instruction to end the processing is given. As the processing is started, in Step S530, the standard image pickup target part data 436 expressing the standard structure of the image pickup target part IT stored in the storage unit 420 is transmitted to the control device 10 by the operation control unit 412 via the communication control unit 417 and the wireless communication unit 470. In Step S532, every time new picked-up image data and position data are stored in the storage unit 420 as the picked-up image data 432 and the position data 433, the picked-up image data and the position data are accumulated in the picked-up image data group 434 by the image pickup target part data creation unit 415 until picked-up image data of a data volume that enables creation/update of image pickup target part data is acquired. Then, if the picked-up image data of the data volume that enables creation/update of image pickup target part data is acquired as the picked-up image data group 434, image pickup target part data expressing the structure of the image pickup target part is created by the image pickup target part data creation unit 415 and stored in the storage unit 420 as the image pickup target part data 435, in Step S536. In Step S538, the image pickup target part data 435 stored in the storage unit 420 is transmitted to the control device 10 by the operation control unit 412 via the communication control unit 417 and the wireless communication unit 470. Then, the processing of creating/updating image pickup target part data in Steps S532 to S538 is executed repeatedly until an instruction to end the processing is given by an end sequence.

As described above, in the endoscope control device 400, after the endoscope device 300 is started up, the image pickup target part data creation/update processing is executed by the operation control unit 412 collaborating with the image pickup target part data creation unit 415 until an instruction to end the processing is given.

Figure 10:
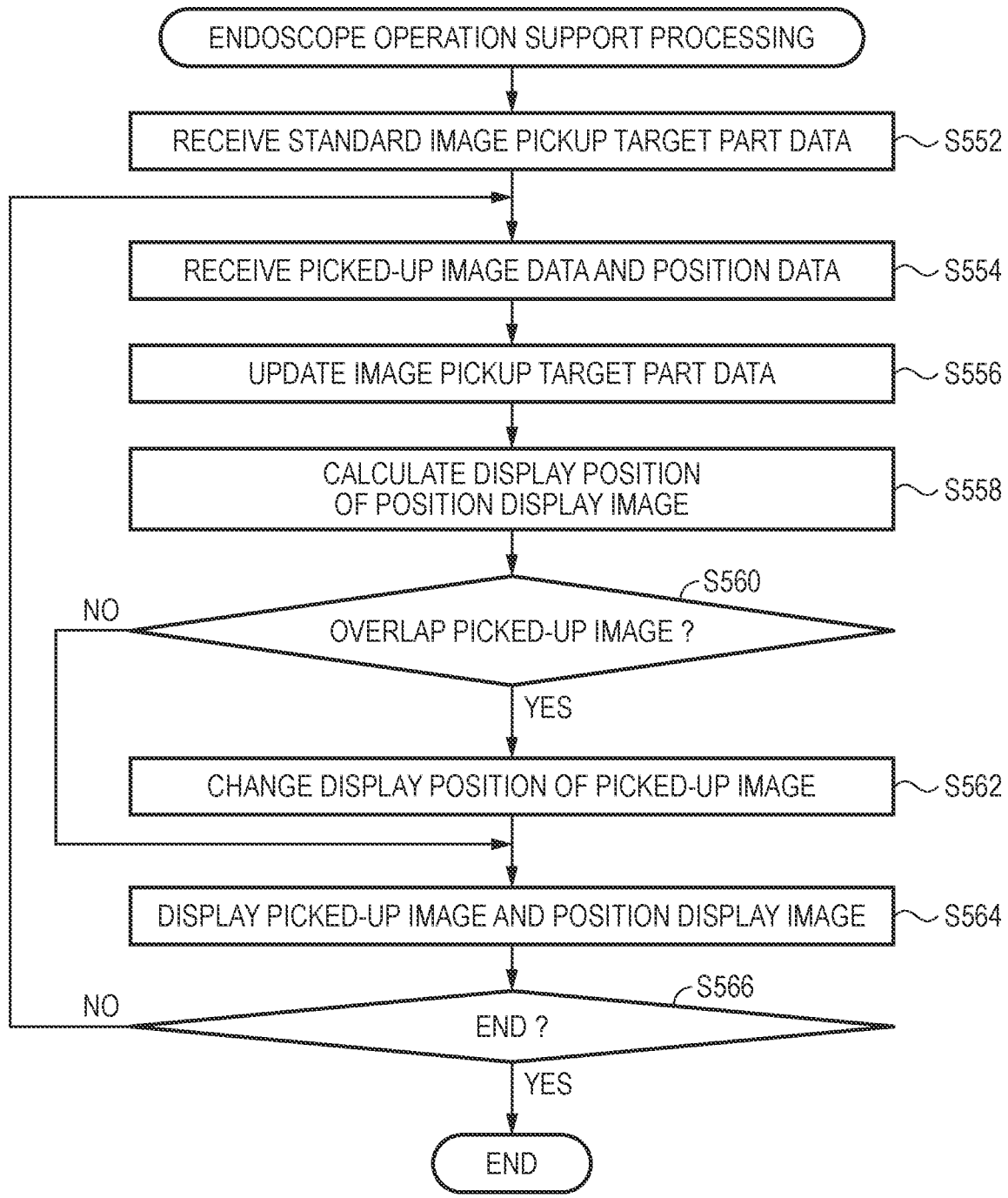
FIG. 10 is a flowchart showing endoscope operation support processing executed in the HMD.

FIG. 10 is a flowchart showing the endoscope operation support processing executed in the HMD 100. The endoscope operation support processing executed in the HMD 100 corresponds to the endoscope operation support unit 157 of the control function unit 150 (FIG. 6). As described above, the endoscope operation support unit 157 is a control unit which function as a computer program (application program) for endoscope operation support stored in the non-volatile storage unit 121 (FIG. 5) is executed by the main processor 140 of the HMD 100. For example, the execution is started in response to the selection being executed, with the direction key 16 (FIG. 1) and the decision key 17 (FIG. 1), of an icon of "endoscope operation support" on a menu screen (not illustrated) displayed as superimposed on the external scenery on the image display unit 20. Thus, wireless communication between the HMD 100 and the endoscope control device 400 is started, and the endoscope operation support processing by the endoscope operation support unit 157 is executed repeatedly until an instruction to end is given by an end sequence.

As the endoscope operation support processing is started, first in Step S552, the endoscope operation support unit 157 receives the standard image pickup target part data that is prepared in advance, from the endoscope control device 400, and stores this data in the storage function unit 122 as the image pickup target part data 125. In Step S554, the endoscope operation support unit 157 receives the picked-up image data and the position data successively transmitted from the endoscope control device 400, and stores these data in the storage function unit 122 as the picked-up image data 127 and the position data 126. If the image pickup target part data is transmitted from the endoscope control device 400, the endoscope operation support unit 157 in Step S556 receives the image pickup target part data and updates the image pickup target part data 125 stored in the storage function unit 122. In Step S558, the endoscope operation support unit 157 calculates the display position of a position display image. However, the processing in Step S556 may be omitted.

Figure 11:
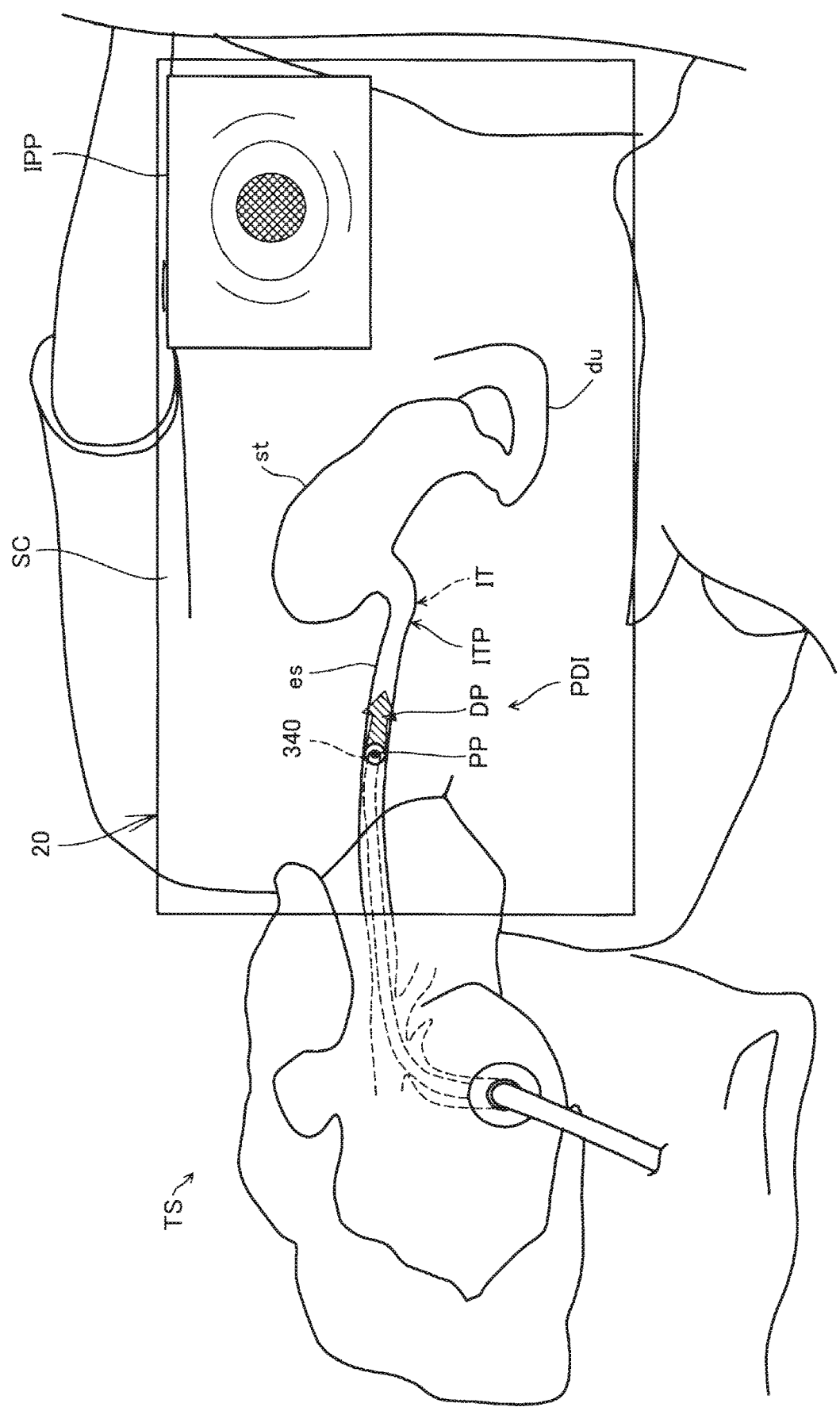
FIG. 11 is an explanatory view showing an example of a position display image displayed on the image display unit.

FIG. 11 is an explanatory view showing an example of a position display image PDI displayed on the image display unit 20. The position display image PDI includes a pointer image PP indicating the position of the distal end part 340, a direction image DP indicating the direction of the distal end part 340, that is, the direction of image pickup by the image pickup unit 342, and an image pickup target part image ITP indicating the image pickup target part IT.

The display position of the image pickup target part image ITP is calculated, for example, as follows. The endoscope operation support unit 157 performs image recognition of an external scenery image picked up by the camera 61 (FIG. 5) and thus extracts the appearance (contour) of the subject (object) TS included in the external scenery in the field of vision of the user. Then, processing such as enlargement, reduction, trimming, or deformation is carried out on the image pickup target part image ITP so that the appearance included in the image pickup target part data 125 matches the extracted appearance. Thus, the display position of the image pickup target part image ITP is calculated. The display position of the pointer image PP is calculated based on the relationship between a reference position of the distal end part 340 and the current position of the distal end part 340, at the display position of the image pickup target part image ITP. The display position of the direction image DP is calculated based on the display position of the pointer image PP and the direction of movement of the distal end part 340.

In Step S560 in FIG. 10, whether the scheduled display position of a picked-up image IPP picked up by the image pickup unit 342 overlaps the display position of the position display image PDI or not is determined. If these display positions overlap each other, the display position of the picked-up image IPP is changed in Step S562. If these display positions do not overlap each other, no change is made to the display position. In Step S564, the picked-up image IPP and the position display image PDI are displayed as virtual images (AR images) on the image display unit 20, as superimposed on the subject TS included in the external scenery SC present in the field of vision, as shown in FIG. 11. Then, the display of the picked-up image IPP and the position display image PDI by the processing in Steps S554 to S564 is executed repeatedly until an instruction to end the processing is given according to an end sequence. If the field of vision of the user US is not directed in the direction of the subject TS and the image pickup target part IT is not present in the field of vision, for example, if the user is looking out at the surroundings, it is preferable that the picked-up image IPP and the position display image PDI are not displayed. Thus, the processing to display AR images is not carried out and therefore processing load can be reduced.

As the image pickup target part image ITP that is displayed, an image covering a range that satisfies a predetermined condition including the current position of the distal end part 340, of the entire image pickup target part included in the image pickup target part data 125, is used. As the predetermined condition, various conditions can be set, for example, an entire image up to the current position of the distal end part 340 (current position) and a range of a predetermined length from the current position, a range of a predetermined length in front of and behind the current position, an entire image up to the current position and a range of organs scheduled to be inspected, and the like, of the image pickup target part IT of the subject TS included in the external scenery SC visually recognized on the image display unit 20. The example of FIG. 11 shows the state where the distal end part 340 is at a halfway part of the esophagus, and where an esophagus image es including the current position of the distal end part 340 (position of the pointer image PP), a stomach image st, and a duodenum image du, of the image pickup target part IT included in the external scenery SC, are displayed.

As described above, the execution of the endoscope operation support processing provides the following effects to the user US operating the endoscope device 300. As shown in FIG. 11, the user US can operate the endoscope unit 310 while confirming, on the position display image PDI, the position where image pickup is being carried out by the image pickup unit 342 of the distal end part 340 inserted in the image pickup target part IT inside the subject TS, and also visually recognizing the picked-up image IPP picked up at that position. Thus, the certainty and safety of the operation of the endoscope device 300 by the user US can be improved.

It is preferable that the image pickup target part image ITP, the pointer image PP, and the direction image DP included in the position display image PDI as an AR image are 3D images with their transmittance and parallax angle adjusted. Particularly, the 3D shapes of the pointer image PP and the direction image DP may be changed according to change in the state of the distal end part 340 (position, speed, direction of movement and the like). Also, the 3D shapes may be changed according to motion parallax generated by the movement or attitude of the head. Using 3D images, it is possible to enhance the sense of reality or the sense of being present at the site and to improve operability. Also, the pointer image PP and the direction image DP are not limited to the shapes shown in FIG. 11. The pointer image PP may be an image in any shape and color or the like, provided that the user US can visually recognize the position of the distal end part 340. The direction image DP may be an image in any shape and color or the like, provided that the user US can visually recognize the direction of and the direction of movement of the distal end part 340. However, the position display image PDI may be a 2D image. Each of the pointer image PP, the direction image DP, and the image pickup target part image ITP may be able to be switched between 2D and 3D.

Figure 12:
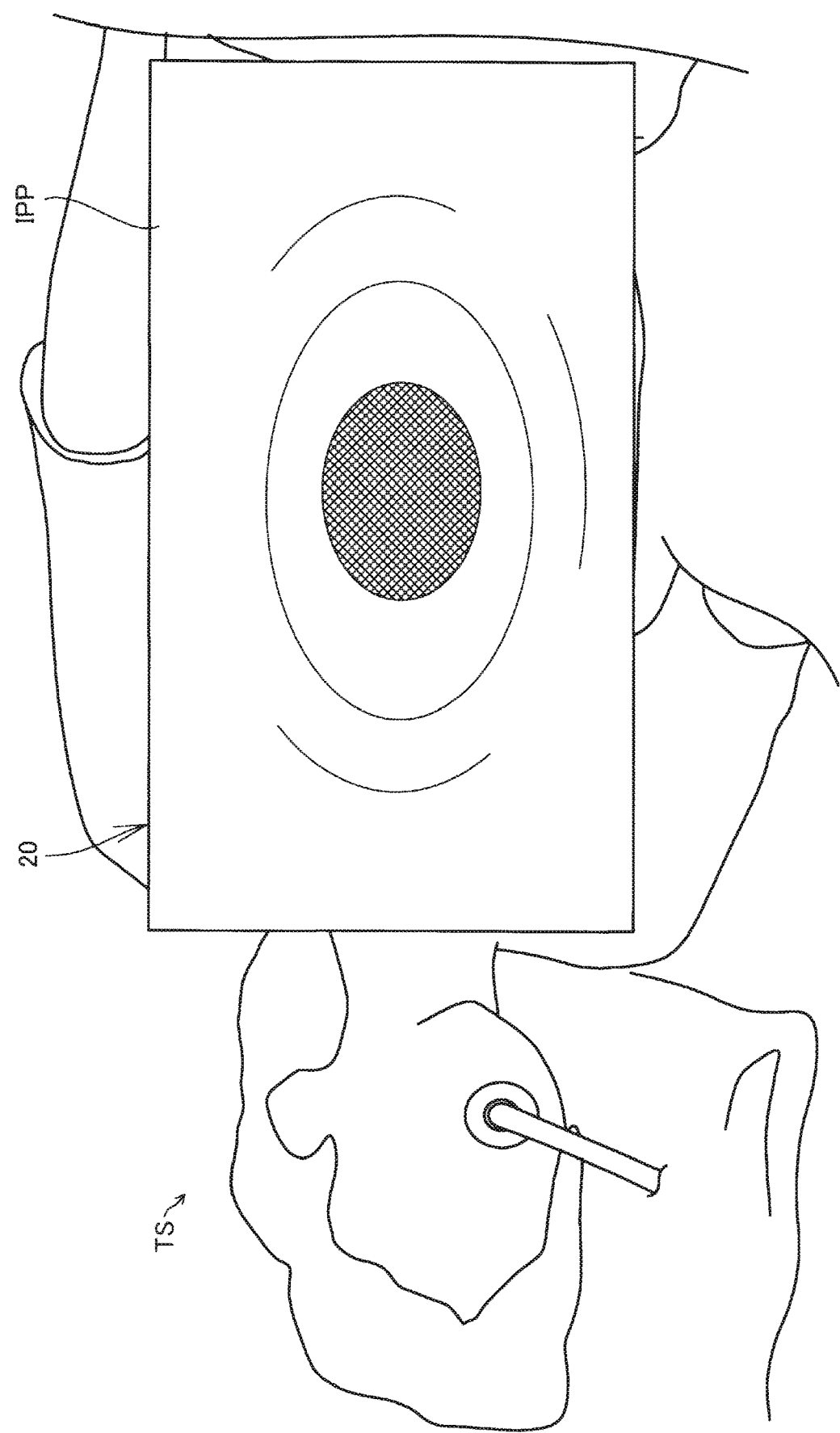
FIG. 12 is an explanatory view showing the state of a full-screen mode in which a picked-up image is displayed on the full screen on the image display unit.

FIG. 12 is an explanatory view showing the state of a full-screen mode where the picked-up image IPP is displayed on a full screen on the image display unit 20. The display of the picked-up image IPP in the full-screen mode may be executed, for example, when it is detected by the endoscope operation support unit 157 that the head of the user US is in a still state where the head remains still for a predetermined period of time, in the state of a see-through mode where the picked-up image IPP and the position display image PDI are displayed as superimposed on the external scenery SC shown in FIG. 11. This still state can be detected based on the state of movement of the head detected by the 6-axis sensor 235 and the magnetic sensor 237 (FIG. 5) provided in the image display unit 20, as described above. However, there are cases where a very small movement of the head may be detected by the sensors and therefore detected as a non-still state, even if the user US thinks that he/she is being still. Thus, it is preferable that a movement within a predetermined range is detected as a still state. Also, the above display may be executed when the position of the distal end part 340 is in a still state. The still state of the position of the distal end part 340 can be determined by detecting a change in the position of the distal end part 340 included in the position data 126. With respect to the still state of the position of the distal end part 340, it is preferable that a change in the position within a predetermined range is detected as a still state, similarly to the case of the head of the user US. As the picked-up image is displayed switching to the full-screen mode, the picked-up image can be visually recognized in an enlarged state and therefore details of the picked-up image can be confirmed. When a movement of the head is detected from the still state, the display mode is switched from the full-screen mode to the see-through mode.

The switching between the see-through mode and the full-screen mode may be carried out in response to a mode switch instruction that is given using the touch pad 14, the direction key 16, and the decision key 17. However, this is not limiting. The switching may be carried out using various other input devices. For example, the switching may be carried out using a wearable device mounted on a hand or foot and capable of giving an instruction according to the movement of the hand or foot.

It is preferable that the picked-up image data group 434 (also referred to as "picked-up image data") in which picked-up image data picked up on a predetermined frame cycle is accumulated, and the image pickup target part data 435 expressing the structure of the image pickup target part created by the image pickup target part data creation unit 415 are outputted to a recording device, not illustrated, via an input/output interface, not illustrated, and are recorded in association with personal information of the subject TS. Thus, the picked-up image expressed by the picked-up image data and the image pickup target part image showing the structure of the image pickup target part can be used for various kinds of analysis (in this example, diagnosis).

The various modifications described above of the first embodiment can also be applied to other embodiments described below.

B. Second Embodiment

Figure 13:
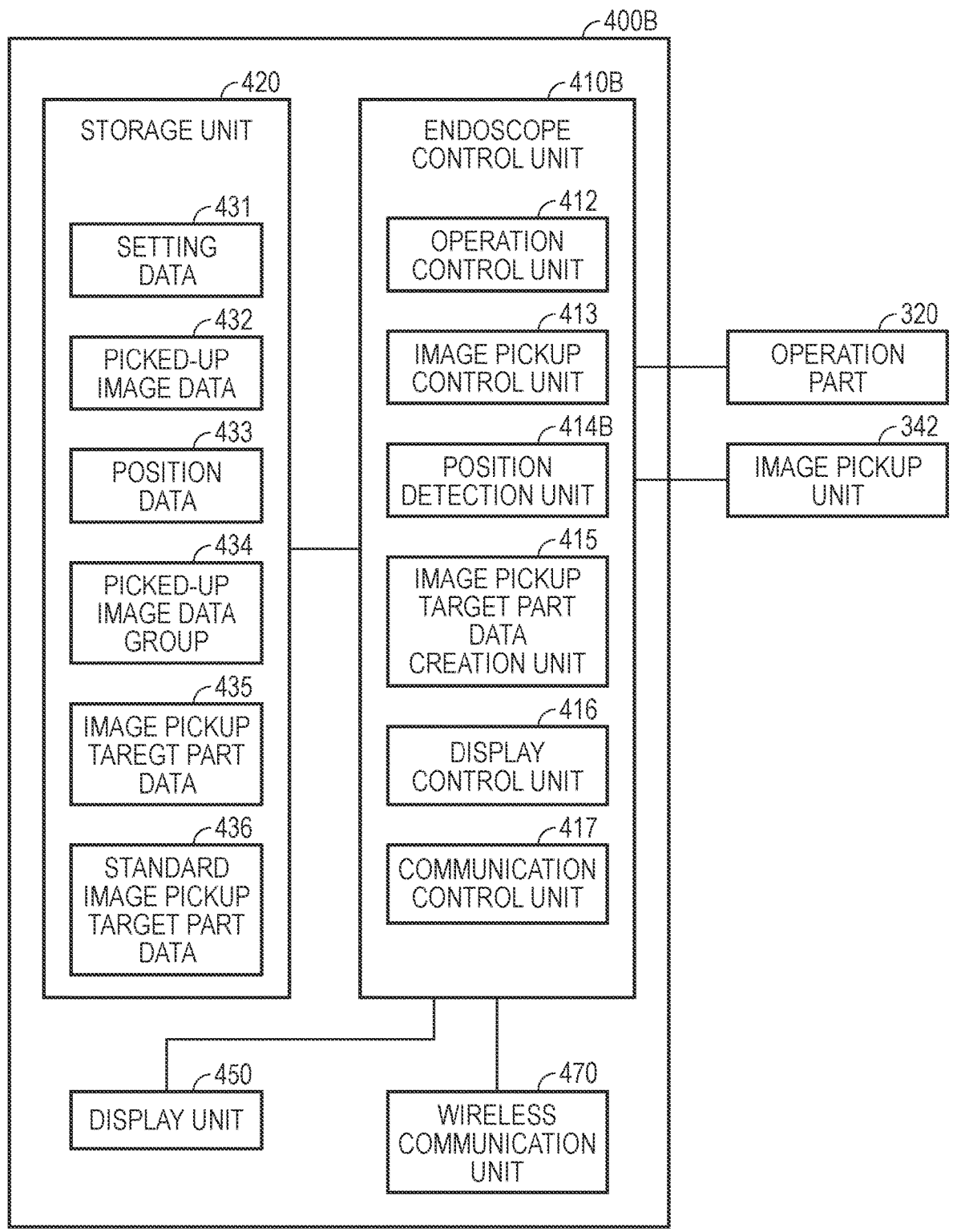
FIG. 13 is a block diagram functionally showing the configuration of an endoscope control device according to a second embodiment.

FIG. 13 is a block diagram functionally showing the configuration of an endoscope control device 400B according to a second embodiment. Similarly to the endoscope control device 400 in the first embodiment, the endoscope control device 400B has an endoscope control unit 410B, a storage unit 420, a display unit 450, a wireless communication unit 470, and a light source generation unit, not illustrated. In the endoscope control unit 410B, the position detection unit 414 (FIG. 7) of the endoscope control unit 410 in the endoscope control device 400 in the first embodiment is replaced by a position detection unit 414B. The other parts of the configuration of the endoscope control device 400B in the second embodiment are the same as those of the endoscope control device 400 in the first embodiment. The position detection unit 414B is not configured to detect the movement of the distal end part 340 with the motion sensor 344 provided at the distal end part 340 as in the endoscope unit 310 in the first embodiment. Instead, the position detection unit 414B is a functional block which detects the position of the distal end part 340 as will be described later, with a configuration without having the motion sensor 344.

Figure 14:
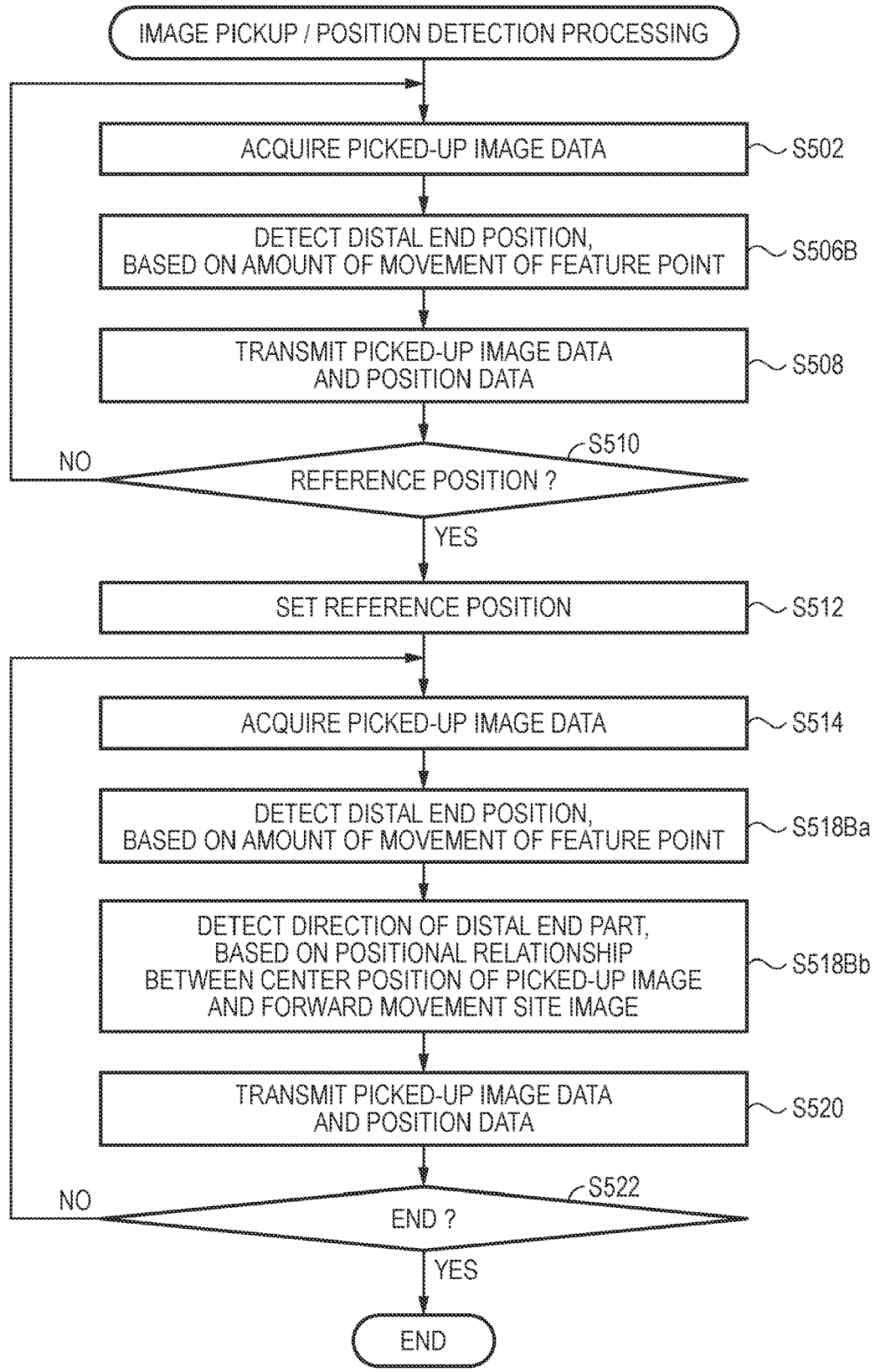
FIG. 14 is a flowchart showing image pickup/position detection processing executed in the endoscope control device.

FIG. 14 is a flowchart showing image pickup/position detection processing executed in the endoscope control device 400B. In this processing, Steps S504 and S516 of the image pickup/position detection processing in the first embodiment are omitted, and Step S506B instead of Step S506, and Steps S518Ba and S518Bb instead of Step S518 are provided. The processing other than Steps S506B, S518Ba and S518Bb is as described in the first embodiment. Therefore, Steps S506B, S518Ba and S518Bb will be described hereinafter.

In Steps S506B and S518Ba, the current position of the distal end part 340 is detected based on the amount of movement of a feature point (amount of change in the position of a feature point).

Figure 15:
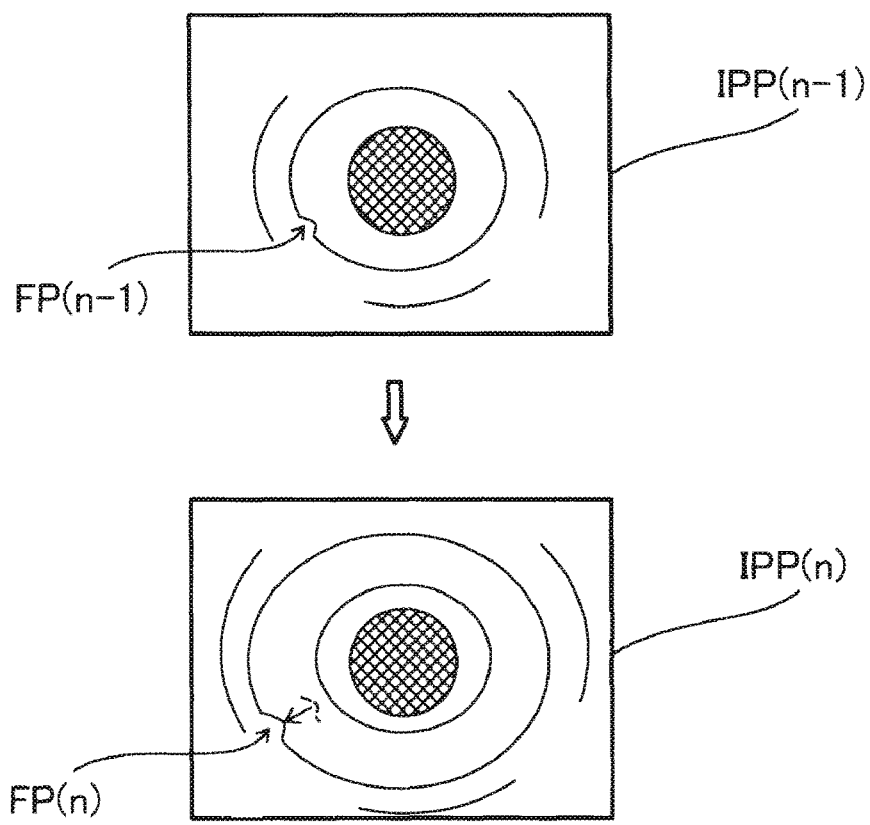
FIG. 15 is an explanatory view showing a method of detecting the position of a distal end part.

FIG. 15 is an explanatory view showing a method for detecting the position of the distal end part 340. It is now assumed that a feature point FP included in a picked-up image IPP expressed by picked-up image data is changed from a feature point FP(n−1) in a picked-up image IPP(n−1) of a frame (n−1) (n being an integer equal to or greater than 0) that is immediately before, as shown at the top of FIG. 15, to a feature point FP (n) in a picked-up image IPP (n) expressed by picked-up image data acquired in the next frame n, as shown at the bottom of FIG. 15. In this case, the change from the position of the feature point FP(n−1) of the frame (n−1) to the position of the feature point FP(n) of the frame n is considered to have happened according to the movement of the position of the distal end part 340. Thus, by calculating the amount of change of the feature point based on the known size of the picked-up image, it is possible to find the amount of movement of the distal end part 340. Then, based on the position of the distal end part 340 in the frame (n−1) and the amount of movement thus found, the position of the distal end part 340 in the frame n, that is, the current position of the distal end part 340 can be detected.

In Step S518Bb, the direction of the distal end surface of the distal end part 340, that is, the direction of image pickup in which image pickup is carried out by the image pickup unit 342 (hereinafter also referred to as the "direction of the image pickup unit 342") is detected, based on the positional relationship between the center position of the picked-up image and a forward movement site image indicating a site where a forward movement can be made, included in the picked-up image. Specifically, this detection can be executed, for example, as follows.

Figure 16:
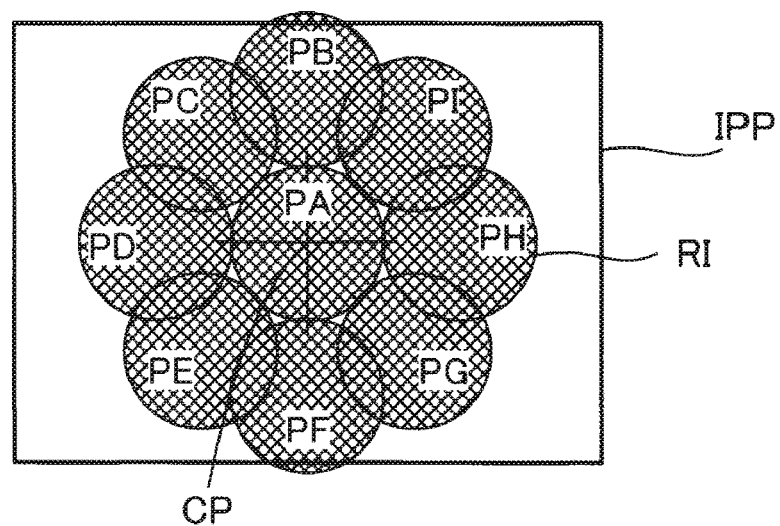
FIG. 16 is an explanatory view showing the state of a forward movement site image in a picked-up image corresponding to the direction of an image pickup unit.
Figure 17:
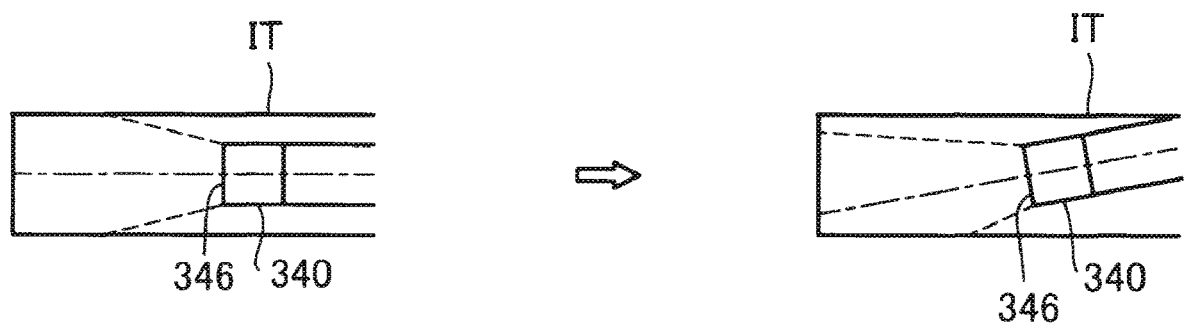
FIG. 17 is an explanatory view showing an example of the direction of the distal end surface of the distal end part in an image pickup target part.

FIG. 16 is an explanatory view showing the state of a forward movement site image RI in the picked-up image IPP corresponding to the direction of the image pickup unit 342. FIG. 17 is an explanatory view showing an example of the direction of a distal end surface 346 of the distal end part 340 inside the image pickup target part IT. As shown in FIG. 16, the position of the forward movement site image RI (illustrated as hatched circles) showing the site (in this example, the tube of a tubular organ) where a forward movement can be made in the image pickup target part IT included in the picked-up image IPP changes as indicated by positions PA to PI with respect to the center position CP of the picked-up image IPP, according to the direction of the distal end surface 346. For example, as shown on the left-hand side of FIG. 17, if the direction of the distal end surface 346 is straight ahead with respect to the path in the image pickup target part IT, the position of the forward movement site image RI is the position PA in FIG. 16. If the direction of the distal end surface 346 changes to an obliquely downward direction from the state of being straight ahead, the position of the forward movement site image RI changes from the position PA to the position PB in FIG. 16. Therefore, for example, according to the positions PA to PI of the forward movement site image RI, the direction of the distal end surface 346 can be detected as follows.

Position PA: the direction of the distal end surface 346 is straight ahead with respect to the path in the image pickup target part IT Position PB: the direction of the distal end surface 346 is obliquely downward with respect to the path in the image pickup target part IT Position PC: the direction of the distal end surface 346 is obliquely downward to the right with respect to the path in the image pickup target part IT Position PD: the direction of the distal end surface 346 is obliquely to the right with respect to the path in the image pickup target part IT Position PE: the direction of the distal end surface 346 is obliquely upward to the right with respect to the path in the image pickup target part IT Position PF: the direction of the distal end surface 346 is obliquely upward with respect to the path in the image pickup target part IT Position PG: the direction of the distal end surface 346 is obliquely upward to the left with respect to the path in the image pickup target part IT Position PH: the direction of the distal end surface 346 is obliquely to the left with respect to the path in the image pickup target part IT Position PI: the direction of the distal end surface 346 is obliquely downward to the left with respect to the path in the image pickup target part IT As the position of the forward movement site image RI moves away from the center position CP, the tilt of the direction of the distal end surface 346 become greater.

As can be understood from the above description, the direction of the distal end surface 346 can be found based on the positional relationship between the center position CP of the picked-up image IPP and the forward movement site image RI indicating the site where a forward movement can be made, included in the picked-up image IPP. However, to simplify the process, it is possible to find the direction of the distal end surface 346 by dividing the picked-up image IPP into m×n (m and n being odd numbers), for example, 3×3 or 5×5 areas, and determining which area the forward movement site image RI is located. Also, the direction of movement can be found, based on the change of the distal end position detected in Step S518Ba and the direction of the distal end surface 346 detected in Step S518Bb.

In the second embodiment, as in the first embodiment, the user US operating the endoscope device can operate the endoscope unit 310 while confirming the position where image pickup is being carried out by the image pickup unit 342 of the distal end part 340 inserted in the image pickup target part IT inside the subject TS, and also visually recognizing the picked-up image picked up at that position.

Thus, the certainty and safety of the operation of the endoscope device can be improved.

C. Third Embodiment

Figure 18:
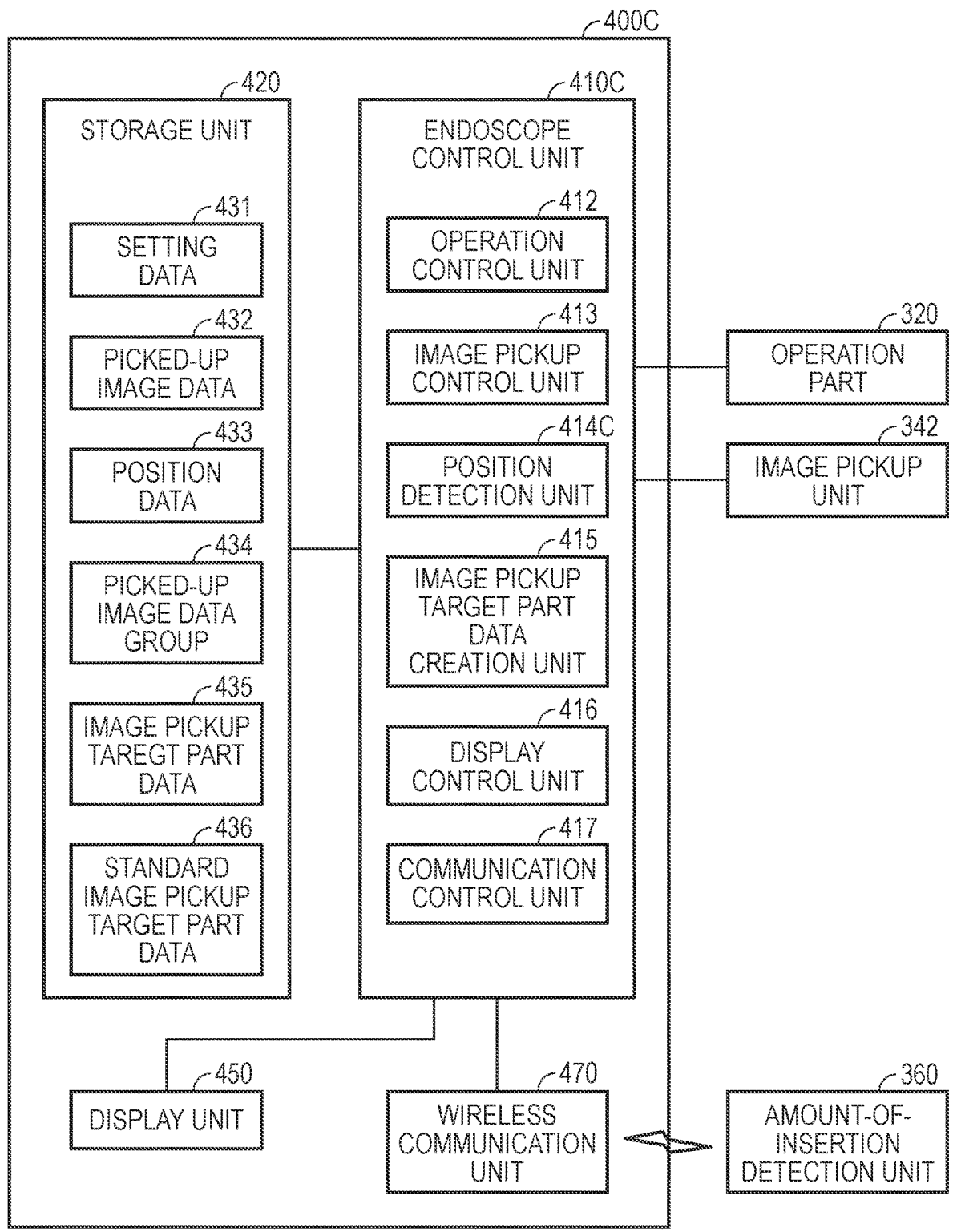
FIG. 18 is a block diagram functionally showing the configuration of an endoscope control device according to a third embodiment.

FIG. 18 is a block diagram functionally showing the configuration of an endoscope control device 400C according to a third embodiment. Similarly to the endoscope control device 400 in the first embodiment, the endoscope control device 400C has an endoscope control unit 410C, a storage unit 420, a display unit 450, a wireless communication unit 470, and a light source generation unit, not illustrated. In the endoscope control unit 410C, the position detection unit 414 (FIG. 7) of the endoscope control unit 410 in the endoscope control device 400 in the first embodiment is replaced by a position detection unit 414C. The other parts of the configuration of the endoscope control device 400C in the third embodiment are the same as those of the endoscope control device 400 in the first embodiment. The position detection unit 414C is a functional block which has an amount-of-insertion detection unit 360 instead of the motion sensor 344 (FIG. 7) and which causes the amount-of-insertion detection unit 360 to detect the amount of insertion of the insertion part 330 (FIG. 1), thus detects the amount of insertion of the distal end part 340, that is, the image pickup unit 342, and detects the position of the distal end part 340, based on the amount of insertion thus detected. The amount-of-insertion detection unit 360 is provided, for example, on a wearing tool mounted on the mouth or nose of the subject TS in order to insert the insertion part 330, and can detect the amount of insertion of the insertion part 330 by reading a scale provided on the insertion part 300. The amount of insertion thus detected is, for example, transmitted from the amount-of-insertion detection unit 360 to the position detection unit 414C via the wireless communication unit 470 and the communication control unit 417 and is used for the detection of the position of the distal end part 340 (image pickup unit 342).

Figure 19:
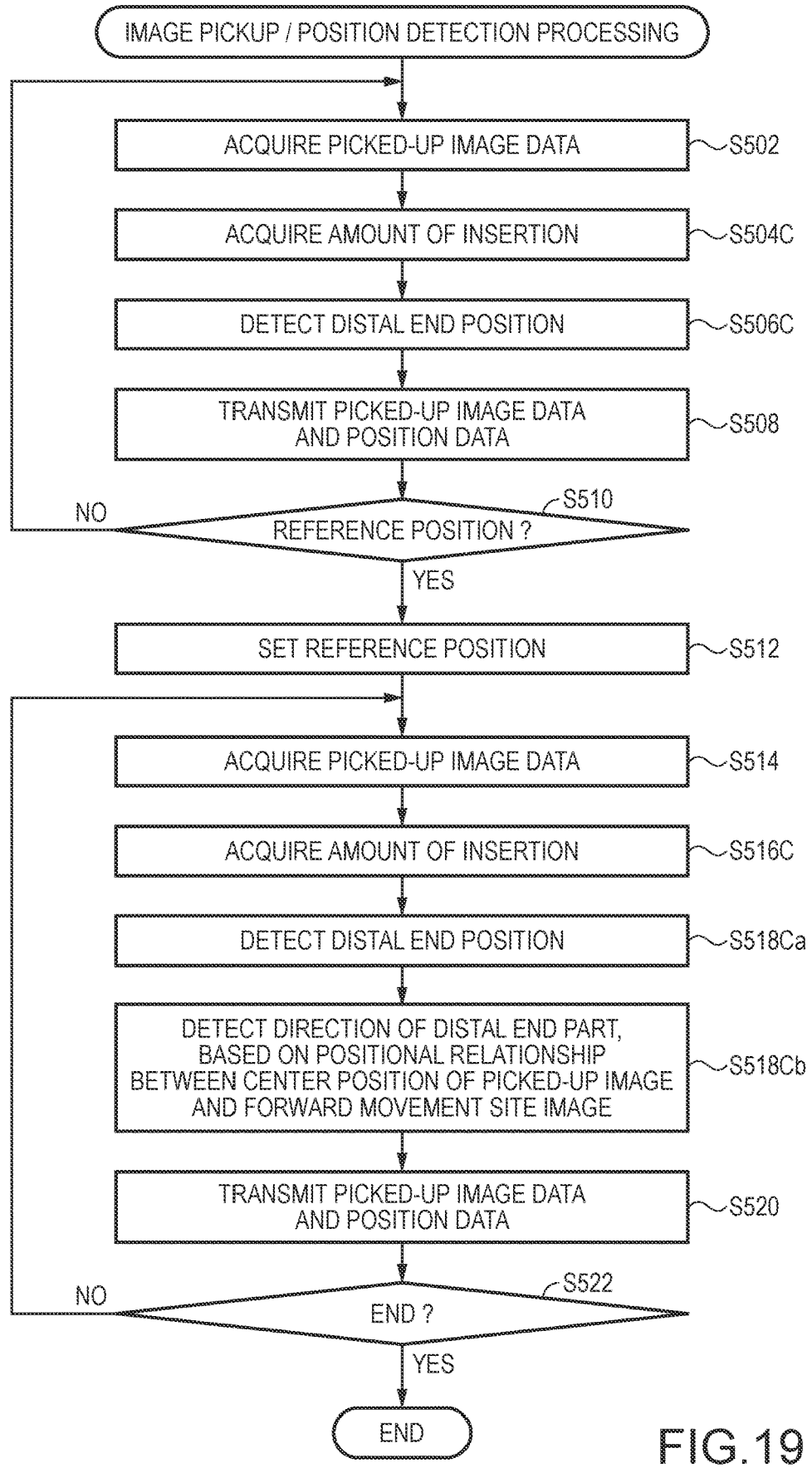
FIG. 19 is a flowchart showing image pickup/position detection processing executed in the endoscope control device.

FIG. 19 is a flowchart showing image pickup/position detection processing executed in the endoscope control device 400C. In this processing, Steps S504C, S506C, and S516C are provided instead of Steps S504, S506, and S516 of the image pickup/position detection processing in the first embodiment showing in FIG. 8, and Steps S518Ca and S518Cb are provided instead of Step S518. The processing other than Steps S504C, 5506C, S516C, S518Ca and S518Cb is as described in the first embodiment. Therefore, Steps S504C, 5506C, S516C, S518Ca and S518Cb will be described hereinafter.

In Steps S504C and S516C, the amount of insertion of the insertion part 330 detected by the amount-of-insertion detection unit 360 is acquired by the position detection unit 414C. In Steps S506C and S518Ca, the current position of the distal end part 340 is detected, based on the reference position and the acquired amount of insertion.

In Step S518Cb, as in Step S518Bb in FIG. 14, the direction of the distal end surface of the distal end part 340, that is, the direction of image pickup in which image pickup is carried out by the image pickup unit 342 (direction of the image pickup unit 342) is detected, based on the center position of the image pickup target part in the picked-up image.

Also, the direction of movement can be detected, based on the change of the distal end position detected in Step S518Ca and the direction of the distal end surface 346 detected in Step S518Cb.

In the third embodiment, as in the first and second embodiments, the user US operating the endoscope device 300 can operate the endoscope unit 310 while confirming the current position where image pickup is being carried out by the image pickup unit 342 of the distal end part 340 inserted in the image pickup target part IT inside the subject TS, and also visually recognizing the picked-up image picked up at that position. Thus, the certainty and safety of the operation of the endoscope device can be improved.

D. Modifications

The invention is not limited to the first, second and third embodiments and their modifications and can be carried out in various other configurations without departing from the scope of the invention. For example, the following modifications are possible.

D1. Modification 1

In the embodiments, the case where the pointer image PP, the direction image DP, and the image pickup target part image ITP are displayed as the position display image PDI is described as an example. However, this is not limiting. It is also possible to display only the pointer image PP as the position display image PDI. Also, the direction image DP may be included in the pointer image PP, and these images may be displayed as a single pointer image.

D2. Modification 2

In the embodiments, it is described that the picked-up image data 432 and the position data 433 acquired on a frame cycle are successively transmitted from the endoscope control device 400 to the control device 10. However, this is not limiting. For example, the picked-up image data 432 and the position data 433 may be transmitted from the endoscope control device 400 to the control device 10 if the amount of movement from the position of the distal end part 340 at the time of the previous transmission changes by a predetermined amount or more. Then, the control device 10 may cause the position display image PDI to be displayed if these data are transmitted thereto. In this case, the amount of data transfer can be reduced and therefore processing load in each device can be reduced.

D3. Modification 3

In the embodiments, it is described that if picked-up image data of a data volume that enables creation/update of image pickup target part data is acquired, image pickup target part data expressing the structure of the image pickup target part is created/updated by the image pickup target part data creation unit 415 of the endoscope control device 400 and transmitted to the control device 10. However, image pickup target part data may be created after all of the picked-up image data over a scheduled range of the image pickup target part is acquired.

D4. Modification 4

In the embodiments, it is described that the determination on a reference position is carried out based on whether a feature part candidate image in an picked-up image expressed by picked-up image data coincides with a feature image of a feature part in an image expressed by standard image pickup target part data expressing a standard structure of the image pickup target part IT. However, this is not limiting. If image pickup target part data is created once for a certain subject TS using the endoscope operation support system, the determination on a reference position may be carried out using the image pickup target part data that is already created, when the endoscope operation support system is used again for the same subject TS. If the image pickup target part data that is already created is recorded in an external recording device, not illustrated, this may be readout and stored in the storage unit 420 for subsequent use.

D5. Modification 5

In the embodiments, the case where a position display image is displayed as superimposed on external scenery transmitted and visually recognized in a see-through manner is described. However, an external scenery image picked up by the camera of the HMD and the position display image may be displayed as superimposed on each other, without transmitting the external scenery.

D6. Modification 6

In the embodiments and modifications, a part of the configurations realized by hardware may be replaced by software. Meanwhile, a part of the configurations realized by software may be replaced by hardware.

D7. Modification 7

In the embodiments, the subject TS (human body) is used as an example of the object in which the insertion part 330 of the endoscope unit 310 is inserted, and a tubular organ is used as an example of the image pickup target part. However, this is not limiting. The invention can be applied to cases where an endoscope device is used for diagnosis on the inside of a human body or for laparoscopic surgery or the like. Also, the invention can be applied not only to the human body but also other living bodies. Moreover, the invention can be applied not only to living bodies but also to cases where an endoscope device is used for inspection or the like on an image pickup target part inside artificial objects as various objects such as water pipe, gas pipe, and electricity pipe within a building or the like.

D8. Modification 8

In the embodiments, an example of the configuration of the HMD is described. However, the configuration of the HMD can be arbitrarily defined without departing from the scope of the invention. For example, addition, deletion, change or the like of components can be made.

In the embodiments, the functional units of the control device 10 and the image display unit 20 are described. However, these can be arbitrarily changed. For example, the following configurations may be employed. A configuration in which the storage function unit 122 and the control function unit 150 are installed in the control device 10, whereas only the display function is provided in the image display unit 20, may be employed. Also, a configuration in which the storage function unit 122 and the control function unit 150 are installed in both of the control device 10 and the image display unit 20 may be employed. Moreover, a configuration in which the control device 10 and the image display unit 20 are unified may be employed. In this case, for example, the image display unit 20 includes all of the components of the control device 10 and is configured as an eyeglasses-type wearable computer. Also, a configuration in which a smartphone or portable game machine is used instead of the control device 10 may be employed. Moreover, a configuration in which the control device 10 and the image display unit 20 are connected together via wireless communication, thus eliminating the connection cable 40, may be employed. In this case, for example, electricity may be wirelessly fed to the control device 10 and the image display unit 20.

D9. Modification 9

The configuration of the control device can be arbitrarily defined without departing from the scope of the invention. For example, addition, deletion, change or the like of components can be made.

In the embodiments, the control function unit 150 operates as the main processor 140 executes a computer program stored in the storage function unit 122. However, the control function unit 150 may employ various configurations. For example, the computer program may be stored in the non-volatile storage unit 121, the EEPROM 215, the memory 118, and other external storage devices (including a storage device such as a USB memory inserted in various interfaces, and an external device such as a server connected via a network), instead of the storage function unit 122 or along with the storage function unit 122. Each function of the control function unit 150 may be realized using an ASIC (application specific integrated circuit) designed to realize the function.

D10. Modification 10

In the embodiments, an example of the configuration of the image display unit is described. However, the configuration of the image display unit may be arbitrarily defined without departing from the scope of the invention. For example, addition, deletion, change or the like of components can be made.

Figure 20:
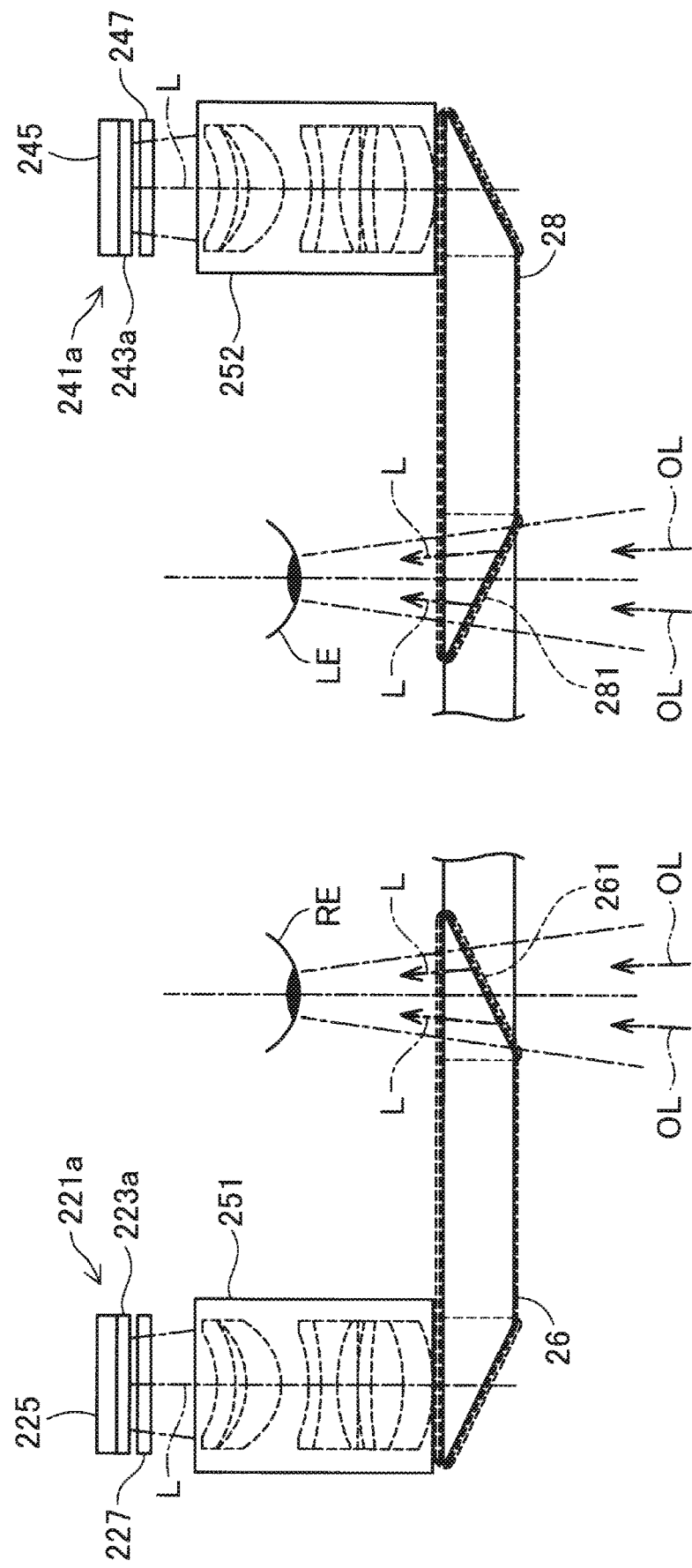
FIG. 20 is a plan view of essential parts showing the configuration of an optical system provided in an image display unit according to a modification.

FIG. 20 is a plan view of essential parts showing the configuration of an optical system provided in an image display unit according to a modification. In the image display unit according to the modification, an OLED unit 221*a* corresponding to the right eye RE of the user and an OLED unit 241*a* corresponding to the left eye LE are provided. The OLED unit 221*a* corresponding to the right eye RE has an OLED panel 223*a* which emits white light, and an OLED drive circuit 225 which drives the OLED panel 223*a* and thus causes the OLED panel 223*a* to emit light. A modulation element 227 (modulation device) is arranged between the OLED panel 223*a* and the right optical system 251. The modulation element 227 is configured of, for example, a transmission-type liquid crystal panel. The modulation element 227 modulates the light emitted by the OLED panel 223*a* and generates image light L. The image light L transmitted and modulated through the modulation element 227 is guided to the right eye RE by the right light guide plate 26.

The OLED unit 241*a* corresponding to the left eye LE has an OLED panel 243*a* which emits white light, and an OLED drive circuit 245 which drives the OLED panel 243*a* and thus causes the OLED panel 243*a* to emit light. A modulation element 247 (modulation device) is arranged between the OLED panel 243*a* and the right optical system 252. The modulation element 247 is configured of, for example, a transmission-type liquid crystal panel. The modulation element 247 modulates the light emitted by the OLED panel 243a and generates image light L. The image light L transmitted and modulated through the modulation element 247 is guided to the left eye LE by the left light guide plate 28. The modulation elements 227, 247 are connected to a liquid crystal driver circuit, not illustrated. This liquid crystal driver circuit (modulation device drive unit) is mounted, for example, on a substrate arranged near the modulation elements 227, 247.

In the image display unit according to the modification, each of the right display unit 22 and the left display unit 24 is configured as a video element having the OLED panel 223a, 243a as a light source unit, and the modulation element 227, 247, which modulates light emitted from the light source unit and outputs image light including a plurality of color lights. The modulation devices for modulating the light emitted from the OLED panels 223a, 243a are not limited to the configuration which employs a transmission-type liquid crystal panel. For example, instead of the transmission-type liquid crystal panel, a reflection-type liquid crystal panel may be used, or a digital micromirror device may be used. Also, a retinal laser projection-type HMD 100 may be employed.

In the embodiments, the eyeglasses-type image display unit 20 is described. However, the configuration of the image display unit 20 can be arbitrarily changed. For example, the image display unit 20 may be configured to be worn like a hat, or may be built in body protection equipment such as a helmet. Also, the image display unit 20 may be configured as an HUD (head-up display) installed in vehicles such as automobile or aircraft, or other transport measures.

In the embodiments, the configuration in which a virtual image is formed by the half mirrors 261, 281 at a part of the right light guide plate 26 and the left light guide plate 28 is described as an example of the optical system which guides image light to the eyes of the user. However, this configuration can be arbitrarily changed. For example, a virtual image may be formed in an area covering the entire surface (or a major part) of the right light guide plate 26 and the left light guide plate 28. In this case, the image may be reduced by an operation of changing the display position of the image. Also, the optical elements in the invention are not limited to the right light guide plate 26 having the half mirror 261 and the left light guide plate 28 having the half mirror 281. An arbitrary configuration using an optical component (for example, diffraction grating, prism, holography or the like) which causes image light to become incident on the eyes of the user can be employed.

The invention is not limited to the foregoing embodiments, examples, and modifications, and can be realized with various configurations without departing from the scope of the invention. For example, technical features of the embodiments, examples, and modifications corresponding to technical features of the respective configurations described in the summary section can be replaced or combined appropriately, in order to solve apart or all of the foregoing problems or in order to achieve a part or all of the foregoing advantageous effects. These technical features can be deleted appropriately, unless described as essential in this specification.

The entire disclosure of Japanese Patent Application No. 2017-013814, filed Jan. 30, 2017 is expressly incorporated by reference herein.

What is claimed is:

1. An endoscope operation support system comprising:
a display which, in the state of being mounted on a head of a user:
transmits external scenery and allows the user to visually recognize the external scenery;
displays a virtual image as superimposed on the external scenery; and
allows the user to visually recognize the virtual image;
an endoscope having an imager at a distal end part inserted in an image pickup target part of an object, the imager picking up an image inside the image pickup target part, the distal end part having an acceleration sensor for detecting a movement of the distal end part;
a position detector which detects a position of the distal end part inserted in the image pickup target part using an amount of movement and a direction of movement of the distal end part obtained from a sensor value of the acceleration sensor; and
a processor which controls the display, the processor being programmed to:
determine whether the distal end position is a reference position by comparing coincidence between the image inside the image pickup target part and a feature image corresponding to the reference position; and
cause the display to display in real-time a position display image including a pointer image indicating the position of the distal end part detected by the position detector, as the virtual image superimposed on the object included in the external scenery.

2. The endoscope operation support system according to claim 1, wherein the position detector finds the position of the distal end part from an amount of change of a position of a feature point included in a picked-up image picked up by the imager.

3. The endoscope operation support system according to claim 1, further comprising:
an amount-of-insertion detector which detects an amount of insertion of the distal end part into the image pickup target part,
wherein the position detector finds the position of the distal end part from the amount of insertion.

4. The endoscope operation support system according to claim 2, wherein the position detector detects a direction of a distal end surface of the distal end part, based on a positional relationship between a center position of a picked-up image picked up by the imager and a forward movement site image showing a site where a forward movement can be made, included in the picked-up image.

5. The endoscope operation support system according to claim 1, wherein the processor is programmed to decide a display position of the position display image in the display, based on a position of the image pickup target part corresponding to a position of the object included in a field of vision of the user, and the detected position of the distal end part.

6. The endoscope operation support system according to claim 1, wherein the processor is programmed to create image pickup target part data expressing a structure of the image pickup target part, using the position of the distal end part detected by the position detector and a picked-up image picked up at the position of the distal end part.

7. The endoscope operation support system according to claim 1, wherein
the image pickup target part is a part that is not shown in an appearance of the object, and the position display image includes the pointer image, an image pickup target part image showing the image pickup target part within a range that satisfies a predetermined condition including the position of the distal end part, and a direction image showing a direction of image pickup by the imager.

8. The endoscope operation support system according to claim 7, wherein the image pickup target part image is created using standard image pickup target part data showing a standard structure of the image pickup target part that is prepared in advance.

9. The endoscope operation support system according to claim 7, wherein before image pickup target part data expressing a structure of the image pickup target part is created, the image pickup target part image is created using standard image pickup target part data showing a standard structure of the image pickup target part that is prepared in advance, whereas in the case where the image pickup target part data is created, the image pickup target part image is created using updated image pickup target part data every time the created image pickup target part data is updated.

10. The endoscope operation support system according to claim 1, wherein the processor is programmed to cause the display to display, as the virtual image, a picked-up image picked up by the imager at the position of the distal end part, in addition to the position display image.

11. The endoscope operation support system according to claim 10, wherein the processor is programmed to cause the display to display the picked-up image at a position that does not overlap with the position display image.

12. The endoscope operation support system according to claim 10, wherein the processor is programmed to:
    switch from a see-through mode in which the position display image and the picked-up image are displayed as the virtual image superimposed on the external scenery, to a full-screen mode in which the picked-up image is displayed on a full screen, if the head is in a still state where the head remains still for a predetermined time; and
    switch to the see-through mode if the head is no longer in the still state.

13. The endoscope operation support system according to claim 10, wherein the processor is programmed to switch between a see-through mode in which the position display image and the picked-up image are displayed as the virtual image superimposed on the external scenery and a full-screen mode in which the picked-up image is displayed on a full screen, in response to a mode switch instruction.

* * * * *